US007589171B2

(12) United States Patent
Bashkin et al.

(10) Patent No.: US 7,589,171 B2
(45) Date of Patent: Sep. 15, 2009

(54) POLYAMIDES FOR TREATING HUMAN PAPILLOMA VIRUS

(75) Inventors: James K. Bashkin, St. Louis, MO (US); Kevin J. Koeller, Richmond Heights, MO (US); Terri Grace Edwards, Kalamazoo, MI (US); Christopher Fisher, Kalamazoo, MI (US)

(73) Assignee: Nanovir, LLC, Kalamazoo, MI (US)

( * ) Notice: Subject to any disclaimer, the term of this patent is extended or adjusted under 35 U.S.C. 154(b) by 0 days.

(21) Appl. No.: 11/800,105

(22) Filed: May 4, 2007

(65) Prior Publication Data

US 2007/0293417 A1    Dec. 20, 2007

Related U.S. Application Data

(63) Continuation of application No. PCT/US2007/06133, filed on Mar. 9, 2007.

(60) Provisional application No. 60/797,426, filed on May 4, 2006.

(51) Int. Cl.
*A61K 38/02* (2006.01)

(52) U.S. Cl. .................. 530/323; 514/13; 548/311.1; 536/25.3; 435/6

(58) Field of Classification Search ................. 530/323; 548/311.1; 536/25.3; 435/6; 514/13
See application file for complete search history.

(56) References Cited

U.S. PATENT DOCUMENTS

| 5,616,606 | A  | 4/1997 | Lown et al. |
| 6,673,940 | B1 | 1/2004 | Dervan et al. |
| 6,958,240 | B1 | 10/2005 | Baird et al. |
| 2003/0109448 | A1 | 6/2003 | Crowley et al. |
| 2003/0119891 | A1 | 6/2003 | Phillion et al. |
| 2004/0171799 | A1 | 9/2004 | Sugiyama et al. |
| 2005/0009054 | A1 | 1/2005 | Phillion et al. |
| 2005/0026174 | A1 | 2/2005 | Dervan et al. |

FOREIGN PATENT DOCUMENTS

| WO | WO-98/35702 | 8/1998 |
| WO | WO-98/37066 | 8/1998 |
| WO | WO-98/37067 | 8/1998 |
| WO | WO-98/50058 | 11/1998 |
| WO | WO-00/15773 | 3/2000 |
| WO | WO-2004/099131 | 11/2004 |
| WO | WO-2005/033282 | 4/2005 |
| WO | WO 2005033282 A2 * | 4/2005 |

OTHER PUBLICATIONS

Schaal et al. Inhibition of human papilloma virus E2 DNA binding protein by covalently linked polyamides. Nucleic Acids Res., 2003; 31(4):p. 1282-1291.*

White et al. Recognition of the Four Watson-Crick base pairs in the DNA minor groove by synthetic ligans. Nature. 1998; 391:p. 468-471.*

Turner et al. Aliphatic/Aromatic Amino Acid pairings for polyamide Recognition in the Minor Groove of DNA. J. Am. Chem. Soc. 1998; 120: p. 6219-6226.*

PCT International Search Report dated Sep. 20, 2007, International Application No. PCT/US2007/006133, for Applicant/Agent File Reference 123918-00005.

Buchmueller, Karen L., et al, Molecular recognition of DNA base pairs by the formamido/pyrrole and formamido/imidazole pairings in stacked polyamides, *Nucleic Acids Research*, 912-921, 2005, vol. 33, No. 3, Oxford University Press.

Coull, Jason J., et al, Targeted Derepression of the Human Immunodeficiency Virus Type 1 Long Terminal Repeat by Pyrrole-Imidazole Polyamides, *Journal of Virology*, Dec. 2002, p. 12349-12354, American Society for Microbiology.

Crowley, Kathleen S., et al, Controlled the Intracellular Localization of Fluorescent Polyamide Analogues in Cultured Cells, *Bioorganic & Medicinal Chemistry Letters* 13 (2003) 1565-1570, Elsevier Science Ltd.

Dervan, Peter B., et al., Recognition of the DNA minor groove by pyrrole-imidazole polyamides, *Current Opinion in Structural Biology* 2003, 13:284-299, Elsevier Science Ltd.

Edelson, Benjamin S., et al, Influence of structural variation on nuclear localization of DNA-binding polyamide-fluorophore conjugates, *Nucleic Acids Research*, 2004, vol. 32, No. 9, pp. 2802-2818, Oxford University Press.

Livengood, Jill A., et al, Paradoxical Effects of DNA Binding Polyamides on HTLV-1 Transcription, *Frontiers in Bioscience* 9, 3058-3067, Sep. 1, 2004.

Lown, J. William, et al, Novel Linked Antiviral and Antitumor Agents Related to Netropsin and Distamycin: Synthesis and Biological Evaluation, *J. Med. Chem.* 1989, 32, 2368-2375, American Chemical Society.

Marques, Michael A., et al, Expanding the Repertoire of Heterocycle Ring Pairs for Programmable Minor Groove DNA Recognition, *J. Am. Chem. Soc.* 2004, 126, 10339-10349, American Chemical Society.

Nickols, Nicholas G., et al, Improved nuclear localization of DNA-binding polyamides, *Nucleic Acids Research*, 2007, vol. 35, No. 2, 363-370.

O'Hare, C. Caroline, et al, DNA sequence recognition in the minor groove by crosslinked polyamides: The effect of N-terminal head group and linker length on binding affinity and specificity, *Proc. Natl. Acad. Sci. USA*, 2002;99;72-77, Jan. 8, 2002 vol. 99 No. 1.

Renneberg, Dorte, et al, Imidazopyridine/Pyrrole and Hydroxybenzimidazole/Pyrrole Pairs for DNA Minor Groove Recognition, *J. Am. Chem. Soc.*, 125, 5707-5716, 2003, American Chemical Society.

(Continued)

*Primary Examiner*—Kamal A Saeed
*Assistant Examiner*—Valerie Rodriguez-Garcia
(74) *Attorney, Agent, or Firm*—Spencer Fane Britt & Browne LLP

(57) ABSTRACT

The present invention relates to polyamide compositions and therapies for treating cells infected with human papilloma virus (HPV).

2 Claims, 8 Drawing Sheets

OTHER PUBLICATIONS

Figure 1:
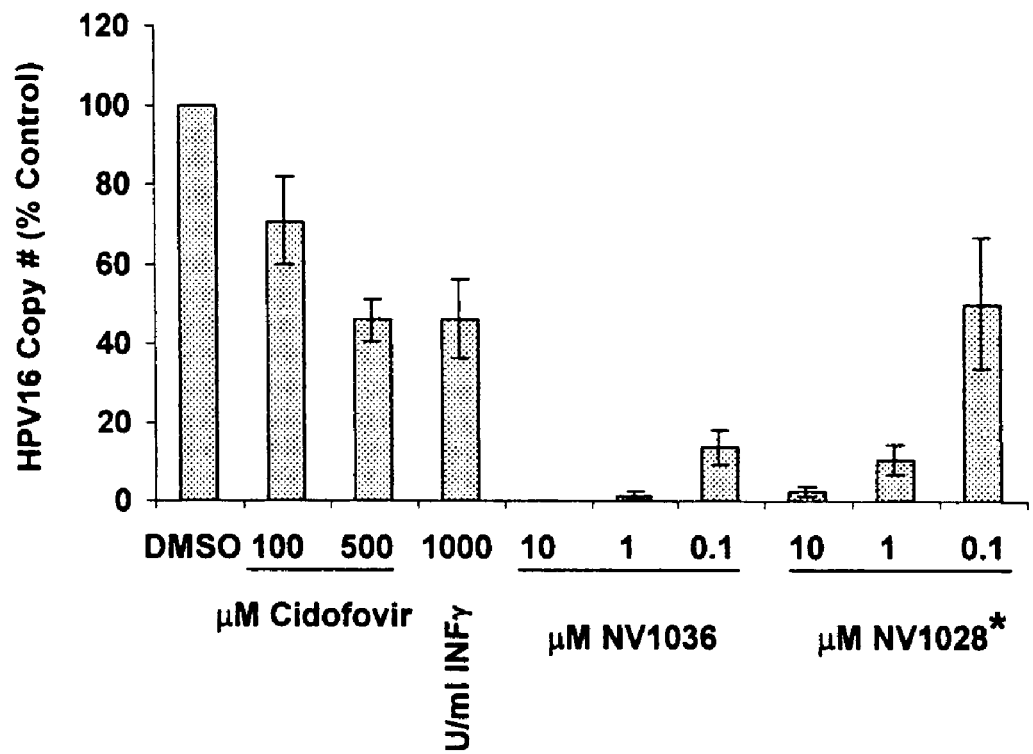

Tsai, Sherry M., et al, Unanticipated differences between α- and γ-diaminobutyric acid-linked hairpin polyamide-alkylator conjugates, *Nucleic Acids Research*, 2007, vol. 35, No. 1, 307-316.

Turner, James M., et al., Aliphatic/Aromatic Amino Acid Pairings for Polyamide Recognition in the Minor Groove of DNA, *J. Am. Chem. Soc.* 1998, 120, 6219-6226, American Chemical Society.

Turner, James M., et al., Recognition of Seven Base Pair Sequences in the Minor Groove of DNA by Ten-Ring Pyrrole—Imidazole Polyamide Hairpins, *J. Am. Chem. Soc.*, 1997, 119, 7636-7644, American Chemical Society.

Schaal, Thomas D., et al, Inhibition of human papilloma virus E2 DNA binding protein by covalently linked polyamides, *Nucleic Acids Research*, 2003, vol. 31, No. 4, pp. 1282-1291, Oxford University Press.

White, Peter W., et al, Inhibition of Human Papillomavirus DNA Replication by Small Molecule Antagonists of the E1-E2 Protein Interaction, *The Journal of Biological Chemistry*, vol. 278, No. 29, Issue of Jul. 18, pp. 26765-26772, 2003, The American Society for Biochemistry and Molecular Biology, Inc.

Zhan, Zheng-Yun J., et al, Alternative Heterocycles for DNA Recognition: A 3-Pyrazole/Pyrrole Pair Specifies for G·C Base Pairs, *Bioorganic & Medicinal Chemistry* 8 (2000) 2467-2474, Elsevier Science Ltd.

Zhang, Wen, et al, Discrimination of Hairpin Plyamides with an β-Substituted-γ-aminobutyric Acid as a 5'-TG-3' Reader in DNA Minor Groove, *J. Am. Chem. Soc.*, 2006, 128, 8766-8776, American Chemical Society.

* cited by examiner

\* In some experiments, HPV episomal copy number was reduced to undetectable levels at concentrations of polyamide as low as 5uM (Q-PCR: 200ng input DNA).

A

B

\* In some experiments, HPV episomal copy number was reduced to undetectable levels at concentrations of polyamide as low as 5uM (Q-PCR: 200ng input DNA).

Im P P β P I P β P P γ(NH₂) P P β P P P β P P P β Ta;

SEQUENCE LISTING

<160> NUMBER OF SEQ ID NOS: 8

<210> SEQ ID NO 1
<211> LENGTH: 34
<212> TYPE: DNA
<213> ORGANISM: Human papillomavirus

<400> SEQUENCE: 1
atgaattatt gtagtttagt attattatat aagt            34

<210> SEQ ID NO 2
<211> LENGTH: 34
<212> TYPE: DNA
<213> ORGANISM: Human papillomavirus

<400> SEQUENCE: 2
acttatataa taatactaaa ctacaataat tcat            34

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
tttggttcag gctggattgc            20

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
gcagatggag cagaacgttt g            21

```
<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
tcgcaagccc accataggcc c                                             21

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
ctgctatttt ggaagattgg aat                                           23

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
ggcctgtgag gtgacaaacc                                               20

<210> SEQ ID NO 8
<211> LENGTH: 27
<212> TYPE: DNA
<213> ORGANISM: Artificial
<220> FEATURE:
<223> OTHER INFORMATION: Primer

<400> SEQUENCE: 8
ttggattgac cacacctccc tcaggtt                                       27
```

POLYAMIDES FOR TREATING HUMAN PAPILLOMA VIRUS

CLAIM OF PRIORITY

This application is a continuation of PCT application No. PCT/US 07/06133, filed on Mar. 9, 2007 and claims the benefit of U.S. Provisional application No. 60/797,426 filed on May 4, 2006, each of which is herein incorporated in its entirety by reference.

FEDERALLY SPONSORED RESEARCH OR DEVELOPMENT

This invention was developed, in part, with government funding under Grant Number R41 A1062182 awarded by the National Institutes of Health. The United States Government may have certain rights in this invention.

TECHNICAL FIELD OF THE INVENTION

The present invention relates to polyamide compositions and therapies for treatment of cells infected with human papilloma virus (HPV).

BACKGROUND OF THE INVENTION

Human papilloma virus is a small double-stranded DNA virus that colonizes various stratified epithelia like skin, oral and genital mucosa, and induces the formation of self-limiting benign tumors known as papillomas (warts) or condylomas. Most of these benign tumors naturally regress due to the influence of host immunological defenses. Some HPVs, however, have oncogenic potential and have been associated with certain types of cancers. See, Lorincz et al., Obstetrics & Gynecology, 79:328-337 (1992); Beaudenon et al., Nature, 321:246-249 (1986); and Holloway et al., Gynecol. Onc., 41:123-128 (1991).

HPV is the most prevalent, sexually transmitted virus. More than 35 HPV genotypes are known to be sexually transmitted, but a relatively few genotypes account for the majority of ano-genital infections. Among these most common HPV types are two forms with high risk for carcinogenic progression (HPV16 and HPV18), and two forms that cause the majority of genital warts (HPV6 and HPV11).

An estimated 5.5 million people become infected with HPV each year in the United States, and an estimated 20 million Americans are currently infected (Cates and et al., Lancet, 354, Suppl. SIV62, 1999). Approximately 75 percent of the male and female reproductive-age population has been infected with sexually transmitted HPV, though the main public health risk is to women through cervical cancer (Koutsky, Am. J. Med., 102(5A), 3-8, 1997). Thus, millions of people in the U.S. alone require treatment each year. It's important to note that PAP smears represent the largest public health screening program in the world, and that the test is, essentially, a measure of HPV infection. The current standard for managing a positive PAP smear is "follow up". In general, no treatment is recommended unless an advanced stage of cervical dysplasia is observed (CDC Sexually Transmitted Diseases Treatment Guidelines, 2002).

Significant need exists in HPV positive patients for effective HPV antiviral drugs. At present no specific treatments exist for HPV or warts. Aldara™ (Imiquimod), a non-specific immunomodulator used for treating external genital warts, is the most successful treatment on the market. An effective, specific HPV treatment has the potential to significantly improve upon, and effectively compete with, Imiquimod.

The majority of human cervical carcinomas (95%) contain and express HPV DNA and it is the expression of two viral oncoproteins, E6 and E7, that appears to be critical for cellular transformation and maintenance of the transformed state. Specifically, four HPV types (HPV-16, HPV-18, HPV-31, and HPV-45) have been connected to 75-93% of the cases of cervical cancer in the United States. It has been estimated that perhaps twenty percent (20%) of all cancer deaths in women worldwide are from cancers that are associated with HPV.

Generally speaking, HPVs are grouped into types based on the uniqueness of their DNA sequence.

HPVs can be further classified as either high or low risk on the basis of the clinical lesions with which they are associated and the relative propensity for these lesions to progress to cancer. Low risk types, such as HPV types HPV-1, HPV-2, HPV-3, HPV-4, HPV-5, HPV-7, HPV-8, and HPV-9 cause common warts (verrucae vulgaris), plantar warts (verrucae plantaris), mosaic warts, flat warts (verrucae plane), and butcher warts. Furthermore, HPV types HPV-6 and HPV-11 cause warts of the external genitalia, anus and cervix. High-risk types, such as HPV-16, HPV-18, HPV-31, HPV-33 and HPV45 are particularly common in intraepithelial carcinomas, neoplasias and cancers. In particular, the genomes of two HPV types, HPV-16 and HPV-18, have been found to be associated with about 70 of invasive carcinomas of the uterine cervix.

Current treatment for HPV infection is extremely limited. Management normally involves physical destruction of the wart by surgical, cryosurgical, chemical, or laser removal of infected tissue. Some of these current treatments, like laser removal and surgery, are expensive and require the use of anesthesia to numb the area to be treated. Cryosurgical removal requires the use of special equipment. Furthermore, most patients experience moderate pain during and after the procedure.

Topical creams and solutions such as preparations of 5-fluorouracil, imiquimod, cidofovir, formaldehyde, glutaral, cimetidine, tricholoroacetic acid, bleomycin, podofilox and podophyllum preparations have also been used. (Reichman in Harrison's 7 Principles of Internal Medicine, 13th Ed. (Isselbacher et al., eds.); McGraw-Hill, Inc., NY (1993) pp. 801-803). Recurrence after these treatments, however, is common, most likely due to the fact that the virus remains latent within the skin cells. Therefore, subsequent repetitive treatments must be used, which can destroy healthy tissue. These treatments are not available or approved for treatment of cervical infections.

Interferon has so far been the most effective treatment for HPV, however, its effectiveness is limited. (Chang et al. (2002) Journal of Virology 76: 8864-74, found some cells infected with HPV genomes became resistant to interferon treatment after only a few applications). See also Cowsert (1994) Intervirol. 37:226-230; Bornstein et al. (1993) Obstetrics Gynecol. Sur. 4504:252-260; Browder et al. (1992) Ann. Pharmacother. 26:42-45.

There is a need for therapeutics for treating a number of diseases and conditions as outlined in this application.

SUMMARY OF THE INVENTION

The present invention provides polyamides, polyamide compositions, and methods for treating HPV infected cells. In some embodiments, the polyamide antiviral agents are well suited for treating laryngeal papillomatosis, cervical dysplasia and cancer and recurrent respiratory papillomatosis (RRP).

In some embodiments, the invention provides a compound of the formula

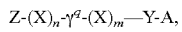

or a pharmaceutically acceptable salt thereof, wherein: m+3 is at least 11; n=m−o; o is 0, 1 or 2; Z is Q-C(O)—; Q can be H, unsubstituted aliphatic, halo-aliphatic, $C_{1-4}$ aliphatic optionally substituted with 1 or 2 amine groups, or a heteroaryl optionally substituted with aliphatic or halo-aliphatic; each X can independently be β-alanine (formula III), 4-amino-2-carbonyl-N-methylpyrrole (formula I), 4-amino-2-carbonyl-N-methylimidazole (formula II), $C_{1-6}$ aliphatic amino acids, natural α-amino acids, formula X1, formula X2, formula X3, formula X4, formula X5, formula X6, formula X7, or formula X8 (Table 1); $\gamma^q$ can be γ-amino butyric acid (formula IV), (R)-2,4-diaminobutyric acid (formula VI), (S)-2,4-diaminobutyric acid, formula γ1, formula γ2, formula γ3, formula γ4 or formula IX,

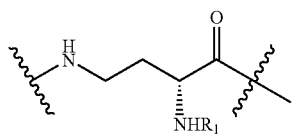

where each $R_1$ can be —C(O)—$R_{1A}$; each $R_{1A}$ can be H, unsubstituted aliphatic or halo-aliphatic; each Y can be β-alanine (formula III), 4-amino-2-carbonyl-N-methylpyrrole (formula I), 4-amino-2-carbonyl-N-methylimidazole (formula II), formula X7, $C_{1-6}$ aliphatic amino acids, or natural α-amino acids; and A can be formula A1, formula A2, formula A3, formula A4, formula A5, formula A6, formula A7, formula A8, formula A9, formula A10, formula A11 or

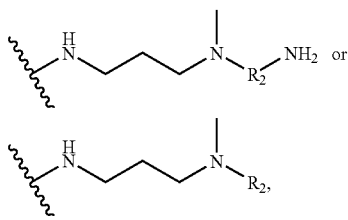

wherein Each $R_2$ is independently $C_{1-5}$ aliphatic.

In one aspect, the total number of 4-amino-2-carbonyl-N-methylimidazole (formula II) units in Z-$(X)_n$-$\gamma^q$-$(X)_m$—Y-A is less than 0.10(m+n+2).

In another aspect, any β-alanine (formula III) unit in Z-$(X)_n$-$\gamma^q$-$(X)_m$—Y-A is adjacent to at least three contiguous units of 4-amino-2-carbonyl-N-methylpyrrole (formula I), at least three contiguous units 4-amino-2-carbonyl-N-methylimidazole (formula II), or at least three contiguous units of any combination of 4-amino-2-carbonyl-N-methylpyrrole (formula I) and 4-amino-2-carbonyl-N-methylimidazole (formula II).

In another embodiment, the compound has the formula

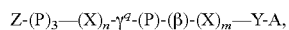

or a pharmaceutically acceptable salt thereof, wherein m+3 is at least 9; and the other substituents are as described above.

In another embodiment, the compound has the formula

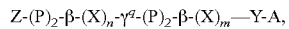

or a pharmaceutically acceptable salt thereof, wherein, m+3 is at least 7 or at least 8; and the other substituents are as described above.

In an aspect of the above embodiments, the total number of 4-amino-2-carbonyl-N-methylimidazole (formula II) units in Z-$(X)_n$-$\gamma^q$-$(X)^m$—Y-A is less than 0.10(m+n+2).

In another aspect of the above embodiments, Q is selected from H, ($C_{1-4}$) aliphatic optionally substituted with 1 to 3 halo, or an optionally substituted monocyclic heteroaryl. Q can also be an optionally substituted imidazole, N-methylimidazole, $CF_3$—, H, $C_{1-4}$ aliphatic optionally substituted with one or two amine groups, Q is a mono or bicyclic heteroaryl, optionally substituted with aliphatic or halo-aliphatic.

In other aspects of the above embodiments, Z can be formulas Z1-17,

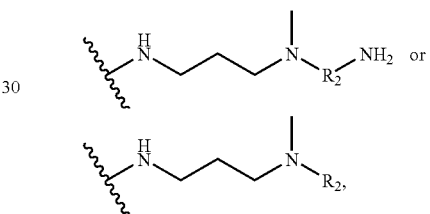

and in some aspects, $R_2$ is $C_{1-3}$ aliphatic.

In other aspects, A can be formulas A1-A11.

In another embodiment, the invention provides a compound comprising the formula

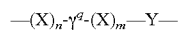

or a pharmaceutically acceptable salt thereof, wherein m+3 is at least 11; and the other substituents are as defined above.

In another embodiment, the invention provides a compound comprising the formula

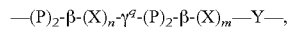

or a pharmaceutically acceptable salt thereof, wherein m+3 is at least 7; and the other substituents are as described above.

In aspects of the above embodiments, $\gamma^q$ is (R)-2,4-diaminobutyric acid (formula VI) and in other aspects, $\gamma^q$ is γ-amino butyric acid (formula IV).

In other aspects of the embodiments, m is an integer between 8 and 11, n is an integer between 6 and 10.

In yet another aspect of the embodiments, Y is β-alanine.

In still another aspect of the embodiments, m is no larger than 25.

In other embodiments, the compound can be:
ImPPβPIPβPPγ($NH^2$)PPβPPPβPPPβTa;
$F_3$CC(O)PPβPPPβPIγ($NH_2$)PβPPPβPPPβPβTa;
$F_3$CC(O)PPβPPPβPγ($NH_2$)PPPβPPPβPβTa;
ImPPβPPPγ($NH_2$)PPβPPPPβTa;
ImPPPβPPPβγPPβPPPβPβTa;
ImPPPβPPPβγ($NH_2$)PPβPPPβPβTa;

ImPPPβPPPγPPPβPPPββTa;
ImPPβPPPγPPβPPPPβTa;
ImPPβPPPγPPβPPPPTa;
ImPPβPPPγ(NH₂)PPβPPPPβTa;
ImPPβPPPγ(NH[C(O)CH₃])PPβPPPPβTa;
ImPPPβPPβγ(NH₂)PPβPPPβPβDp;
ImPPβPPPβPPPγ(NH₂)PPPβPPPβPPPβDp;
ImPPβPPPγPPβPPPPβDp;
ImPPPβPPPβPPPγPPPβPPPβP ments, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propel, isopropyl, butyl, isobutyl, sec-butyl, tart-butyl, n-pentyl, n-hepty or 2-ethylhexyl. An alkyl group can be substituted (i.e., optionally substituted) with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, or heterocycloaliphaticamino]; sulfonyl [e.g., aliphatic-S(O)$_2$—]; sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroarylalkoxy; alkoxycarbonyl; alkylcarbonyloxy; or hydroxy. Without limitation, some examples of substituted alkyls include carboxyalkyl (such as HOOC-alkyl, alkoxycarbonylalkyl, and alkylcarbonyloxyalkyl); cyanoalkyl; hydroxyalkyl; alkoxyalkyl; acylalkyl; aralkyl; (alkoxyaryl)alkyl; (sulfonylamino)alkyl (such as alkyl-S(O)$_2$-aminoalkyl); aminoalkyl; amidoalkyl; (cycloaliphatic)alkyl; or haloalkyl.

As used herein, a halo-aliphatic group refers to an aliphatic group that is substituted with 1-3 halo atoms, wherein aliphatic and halo are defined herein. Substitution can occur at any chemically feasible carbon atom.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl and 2-hexenyl. An alkenyl group can be optionally substituted with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, heterocycloaliphaticamino, or aliphaticsulfonylamino]; sulfonyl [e.g., alkyl-S(O)$_2$—, cycloaliphatic-S(O)$_2$—, or aryl-S(O)$_2$—]; sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroaralkoxy; alkoxycarbonyl; alkylcarbonyloxy; or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-S(O)$_2$-aminoalkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl; heteroaroyl; alkoxy; cycloalkyloxy; heterocycloalkyloxy; aryloxy; heteroaryloxy; aralkyloxy; nitro; carboxy; cyano; halo; hydroxy; sulfo; mercapto; sulfanyl [e.g., aliphatic-S— or cycloaliphatic-S—]; sulfinyl [e.g., aliphatic-S(O)— or cycloaliphatic-S(O)—]; sulfonyl [e.g., aliphatic-S(O)$_2$—, aliphaticamino-S(O)$_2$—, or cycloaliphatic-S(O)$_2$—]; amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl]; urea; thiourea; sulfamoyl; sulfamide; alkoxycarbonyl; alkylcarbonyloxy; cycloaliphatic; heterocycloaliphatic; aryl; heteroaryl; acyl [e.g., (cycloaliphatic)carbonyl or (heterocycloaliphatic)carbonyl]; amino [e.g., aliphaticamino]; sulfoxy; oxo; carbamoyl; (cycloaliphatic)oxy; (heterocycloaliphatic)oxy; or (heteroaryl)alkoxy.

As used herein, an "amido" encompasses both "aminocarbonyl" and "carbonylamino". These terms when used alone or in connection with another group refers to an amido group such as —N(R$^X$)—C(O)—R$^Y$ or —C(O)—N(R$^X$)$_2$, when used terminally, and —C(O)—N(R$^X$)— or —N(R$^X$)—C (O)— when used internally, wherein R$^X$ and R$^Y$ are defined below. Examples of amido groups include alkylamido (such as alkylcarbonylamino or alkylaminocarbonyl), (heterocycloaliphatic)amido, (heteroaralkyl)amido, (heteroaryl) amido, (heterocycloalkyl)alkylamido, arylamido, aralkylamido, (cycloalkyl)alkylamido or cycloalkylamido.

As used herein, an "amino" group refers to —NR$^X$R$^Y$ wherein each of R$^X$ and R$^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic) carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings.

For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [ e.g., aliphaticcarbonyl, (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl]; sulfonyl [e.g., aliphatic-$S(O)_2$— or amino-$S(O)_2$—]; sulfinyl [e.g., aliphatic-S(O)— or cycloaliphatic-S(O)—]; sulfanyl [e.g., aliphatic-S-]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl) aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy) alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl]; cycloaliphatic [e.g., cycloalkyl or cycloalkenyl]; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino]; cyano; halo; hydroxy; acyl; mercapto; alkylsulfanyl; sulfoxy; urea; thiourea; sulfamoyl; sulfamide; oxo; or carbamoyl.

As used herein, a "bicyclic ring system" includes 8-12 (e.g., 9, 10 or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2] octyl, bicyclo[3.3.1]nonyl, bicyclo[3.3.2.]decyl, bicyclo [2.2.2]octyl, adamantyl, azacycloalkyl or ((aminocarbonyl) cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl]; cycloaliphatic; (cycloaliphatic) aliphatic; heterocycloaliphatic; (heterocycloaliphatic) aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl]; cyano; halo; hydroxy; mercapto; sulfonyl [e.g., alkyl-$S(O)_2$— and aryl-$S(O)_2$—]; sulfinyl [e.g., alkyl-S(O)—]; sulfanyl [e.g., alkyl-S—]; sulfoxy; urea; thiourea; sulfamoyl; sulfamide; oxo; or carbamoyl.

As used herein, "cyclic moiety" includes cycloaliphatic, heterocycloaliphatic, aryl or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b] thiopheneyl, 2-oxa-bicyclo[2.2.2]octyl, 1-aza-bicyclo[2.2.2] octyl, 3-aza- bicyclo[3.2.1 ]octyl, anad 2,6-dioxa-tricyclo [3.3.1.0$^{3,7}$]nonyl. A monocyclic heterocycloalkyl group can be fused with a phenyl moiety to form a heteroaryl such as tetrahydroisoquinoline. A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl]; nitro; cyano; halo; hydroxy; mercapto; sulfonyl [e.g., alkylsulfonyl or arylsulfonyl]; sulfinyl [e.g., alkylsulfinyl]; sulfanyl [e.g., alkylsulfanyl]; sulfoxy; urea; thiourea; sulfamoyl; sulfamide; oxo; or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl,cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H- indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [ e.g., aliphaticcarbonyl; (cycloaliphatic)carbonyl; ((cycloaliphatic)aliphatic)carbonyl; (araliphatic)carbonyl; (heterocycloaliphatic) carbonyl; ((heterocycloaliphatic)aliphatic)carbonyl; or (heteroaraliphatic)carbonyl]; sulfonyl [e.g., aliphatic-S(O)$_2$— or amino-S(O)$_2$—]; sulfinyl [e.g., aliphatic-S(O)—]; sulfanyl [e.g., aliphatic-S—]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; [((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (e.g., carboxyalkyl, hydroxyalkyl, and haloalkyl such as trifluoromethyl); alkenyl; alkynyl; cycloalkyl; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; aminocarbonyl; alkylcarbonylamino; cycloalkylcarbonylamino; (cycloalkylalkyl)carbonylamino; arylcarbonylamino; aralkylcarbonylamino; (heterocycloalkyl)carbonylamino; (heterocycloalkylalkyl)carbonylamino; heteroarylcarbonylamino; heteroaralkylcarbonylamino; cyano; halo; hydroxy; acyl; mercapto; alkylsulfanyl; sulfoxy; urea; thiourea; sulfamoyl; sulfamide; oxo; or carbamoyl.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO— $NR^XR^Y$ or —$NR^X$—CO—O—$R^Z$ wherein $R^X$ and $R^Y$ have been defined above and $R^Z$ can be aliphatic, aryl, aralyphatic, heterocycloaliphatic, heteroaryl or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$ and R$^Z$ have been defined above.

As used herein, a "sulfamoyl" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$ and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to -S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$-or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refers to —C(O)—.

As used herein, an "oxo" refers to =O.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$ and R$^Z$ have been defined above.

As used herein, a "guanidine" group refers to the structure —N=C(N(R$^X$R$^Y$))N(R$^X$R$^Y$) wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, the term "amidino" group refers to the structure —C=(NR$^X$)N(R$^X$R$^Y$) wherein R$^X$ and R$^Y$ have been defined above.

As used herein, "cyclic group" includes mono-, bi- and tri-cyclic ring systems including cycloaliphatic, heterocycloaliphatic, aryl or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1 ]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$— where Q is hydrogen or an aliphatic group; however, Q shall be an aliphatic group in at least one instance. The term aliphatic chain includes alkyl chains, alkenyl chains, and alkynyl chains, where alkyl, alkenyl and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables contained herein encompass specific groups, such as alkyl and aryl. Unless otherwise noted, each of the specific groups can be optionally substituted with one or more substituents described herein. Each substituent of a specific group is further optionally substituted with one to three of halo, cyano, oxoalkoxy, hydroxy, amino, nitro, aryl, haloalkyl and alkyl. For instance, an alkyl group can be substituted with alkylsulfanyl and the alkylsulfanyl can, in turn, be optionally substituted with one to three of halo, cyano, oxoalkoxy, hydroxy, amino, nitro, aryl, haloalkyl and alkyl. As an additional example, the cycloalkyl portion of a (cycloalkyl)carbonylamino can be optionally substituted with one to three of halo, cyano, alkoxy, hydroxy, nitro, haloalkyl and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. The compounds of this invention may function in protonated (cationic) forms and may cross membranes in neutral forms.

As used herein, an effective amount is defined as the amount required to confer a therapeutic effect on the treated patient, and is typically determined based on age, surface area, weight and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

II. Chemical Background

Certain oligomers of nitrogen heterocycles can be used to bind to particular regions of double stranded DNA. Particularly, N-methyl imidazole (I), des-amino-N-methyl imidazole (Im), and N-methyl pyrrole (P) have a specific affinity for particular bases. This specificity can be modified based upon the order in which these compounds are linked. It has been shown that there is specificity in that G/C is complemented by Im/P or I/P, C/G is complemented by P/Im or P/I, and A/T and T/A are redundantly complemented by P/P.

In effect, N-methyl imidazole and des-amino-N-methyl imidazole tend to be associated with guanine, while N-methyl pyrrole is associated with cytosine, adenine and thymine. By providing for two chains of the heterocycles, as 1 or 2 molecules, a 2:1 complex with double stranded DNA is formed, with the two chains; of the oligomer antiparallel, where G/C pairs have Im/P or I/P in juxtaposition, C/G pairs have P/Im or P/I, and T/A pairs have P/P in juxtaposition. The heterocycle oligomers are joined by amide (carbamyl) groups, where the NH may participate in hydrogen bonding with nitrogen unpaired electrons, particularly of adenine.

Polyamides may be synthesized to form hairpin compounds by incorporating compounds, such as gamma-aminobutyric acid (γ) or gamma- amino-beta-aminobutyric acid (γNH$_2$), to allow a single polyamide to form a complex with DNA. Such a structure has been found to significantly increase the binding affinity of the polyamide to a target sequence of DNA.

Beta-alanine (β) may be substituted for a pair of N-methyl pyrrole groups when an AT or TA base pair is the target sequence. The added flexibility of the beta-alanine can help the entire polyamide stay "in register" with the target sequence of DNA.

In some embodiments, the polyamide molecule begins with des- amino-N-methyl imidazole which has a specific affinity for guanosine. In other embodiments, the polyamide molecule ends with either 3-(Dimethylamino) propylamine (Da) or 3,3'-Diamino-N-methyldipropylamine (Ta). Dye molecules can be incorporated at the amino groups of the γ-amino-butyric acid, the Ta, or at both of these sites if both are available in the same molecule.

More recently it has been discovered that the inclusion of a new aromatic amino acid, 3-hydroxy-N-methylpyrrole (Hp), when incorporated into a polyamide and paired opposite Py, provides the means to discriminate A-T from T-A. White S., et al., Nature 391, 436-38 (1998). Unexpectedly, the replacement of a single hydrogen atom on the pyrrole with a hydroxy group in an Hp/P pair regulates the affinity and the specificity of a polyamide by an order of magnitude. Using Hp together with P and Im or I in polyamides to form six aromatic amino acid pairs (I/P, Im/P, P/Im, P/I, Hp/P and P/Hp) provides a code to distinguish all four Watson-Crick base pairs in the minor groove of DNA in environments in which Hp does not decompose.

Naturally occurring pyrrole-containing polyamides such as distamycin and netropsin, as well as their pyrrole/imidazole-containing synthetic analogs, bind with high affinity to the minor groove of DNA. Direct evidence of specific polyamide-DNA binding has been extensively reported by the Dervan group using X-ray crystallography, NMR structure determinations and quantitative affinity cleavage methods (Baird and Dervan, 1998; Pilch et al., Biochemistry, 38, 2143-51, 1999; Pilch et al., Proc. Natl. Acad. Sci. USA, 93, 8306-11 1996; Wang, Ellervik, and Dervan, Bioorg. Med. Chem., 9, 653-7, 2001; White, Baird, and Dervan, Biochemistry, 35, 12532-27, 1996; White, Baird, and Dervan, Chem. Biol., 4, 569-78, 1997, all of which are incorporated herein by reference). Because of the H-bonding scheme, synthetic polyamides can be designed to recognize specific DNA sequences.

The rules for DNA recognition by polyamides are summarized in the following paragraphs (White, Baird, and Dervan, Chem. Biol., 4, 569-78, 1997). Pyrrole (typically abbreviated Py or P, ) binds to the three nucleotides that present hydrogen bond acceptors in the minor groove, or A, T and C (Kielkopf et al., Science, 282, 111-5, 1998; Kielkopf, et al., Nat. Struct. Biol., 5, 104-9, 1998; Melander, Herman, and Dervan, Chemistry, 6, 4487-97, 2000, all of which are incorporated herein by reference). These nucleotides present only hydrogen bond acceptors to the minor groove: A and C each offer one lone pair of electrons while T offers two lone pairs from the carbonyl oxygen bound to C2. It is the amide NH of the hairpin pyrrole amino acids that is the hydrogen bond donor. So, the pyrrole ring acts as a curved spacer that presents amide NHs at the correct distance and curvature to match up with the pattern of hydrogen bond acceptors presented by A,C and T when located in B-form DNA. Imidazole (Structure II below) is typically abbreviated I.

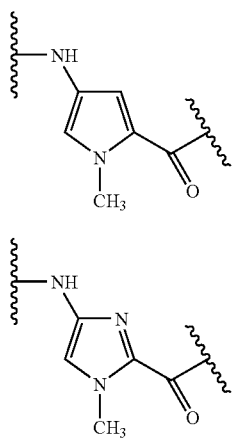

I (P)

II (I)

Additional polyamide building blocks and binding rules can be found in (Urbach et al., J. Mol. Biol., 320, 55-71, 2002; Wang, Ellervik, and Dervan, Bioorg. Med. Chem., 9, 653-57, 2001, both of which are incorporated herein by reference). However, these studies showed that β-alanine (Structure III (β), below) can act as an H-bond donor that is selective for A,T and C.

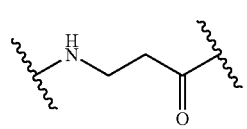

III (β)

For additional recognition, the γ-amino butyric acid (Structure IV (γ) below) building block used to form the hairpin turn (See FIG. 5) was found to bind A/T, but not G/C, base pairs. Similar preference for A/T over G/C base pairs is shown for the positively-charged amino tail that is present in most polyamides. This mimics the cationic guanidine group in distamycin. (Parks, Baird, and Dervan, 1996; Pilch et al., Proc. Natl. Acad. Sci. USA, 93, 8306-11, 1996; Trauger et al., Chem. Biol., 3, 369-77, 1996; Urbach and Dervan, Proc. Natl. Acad. Sci. USA, 98, 4343-48, 2001; Urbach et al., J. Mol. Biol., 320, 55-71, 2002; Wang, Ellervik, and Dervan, Bioorg. Med. Chem., 9, 653-57, 2001, each of which is incorporated herein by reference). Standard hairpin polyamides show the highest affinity for sequences that begin 5'—WWG-3', where W═A or T.

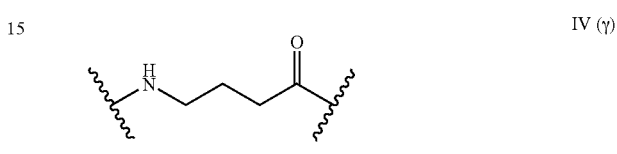

IV (γ)

Other building blocks include, without limitation, desamino-imidazole (Formula V (Im)), ((R)-2,4-diaminobutyric acid (Formula VI, γNH$_2$)), 3-(dimethylamino)propylamine (Formula VII, Dp) and 3, 3'-diamino-N-methyldipropylamine (formula VIII, Ta).

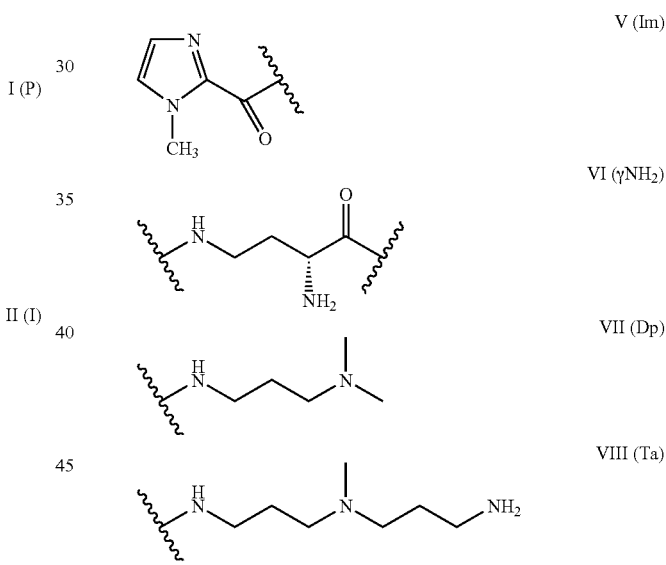

V (Im)

VI (γNH$_2$)

VII (Dp)

VIII (Ta)

Polyamide-DNA binding has been reported to interfere with protein-DNA binding (Fechter and Dervan, J. Am. Chem. Soc., 125, 8476-85, 2003; Nguyen-Hackley et al., Biochemistry, 43, 6880-90, 2004; Schaal et al., Nucl. Acids Res., 31, 1282-91, 2003, all of which are incorporated herein by reference), and polyamides have been reported to inhibit gene expression, presumably through competition with transcription factors for DNA binding sites (Dickinson et al., Biochemistry, 38, 10801-7, 1999; Supekova et al., Chem. Biol., 9, 821-7, 2002; Weisz, 1997, all of which are incorporated herein by reference). The expression of eukaryotic genes is dependent on the formation of an active transcription complex whose components are highly variable and promoter/gene dependent. Of primary importance in the assembly of a transcription complex is the binding of transcription factors to their associated consensus sequences. While many genes share transcription factors (TFs), the combination of a specific TF binding site with the adjacent DNA unique to a target gene may provide a relatively unique site within the human genome. Thus, by designing polyamides to recognize a TF binding site and some adjacent DNA, it has been possible to target the promoter region of a unique gene even if the TF has binding sites in the control regions of many genes.

III. HPV Targets

The present invention provides polyamides and analogs of polyamide polymers that are useful for treating HPV infections and other diseases. Without wishing to be bound by any particular theory, the anti-HPV activity of polyamides provides information for predicting and developing general rules for designing polyamides against all HPV subtypes, and to other double-stranded DNA viruses. The methodology is useful in predicting which polyamide structures will possess broad-spectrum anti-viral activity against other double-stranded DNA viruses, including Epstein-Barr viruses, herpes viruses and pox viruses.

Time-course experiments of the anti-HPV action of the polyamides of this invention led to the discovery that certain active molecules decrease HPV DNA levels in human keratinocytes by >90% in as short as 30 min after drug treatment.

HPV DNA anchors itself to human chromosomes. The various reasons for this include a need for close proximity to human DNA replication elements for viral replication and nuclear maintenance of episodes and proper segregation of viral episodes into daughter cells during cell division. In addition, while the processes are poorly understood, viral genomes must evade innate immune systems that recognize and eliminate foreign, or non-self, DNA.

Without being bound by theory, it is possible that polyamides of the present invention are capable of either displacing the circular HPV genome from the host chromosomes resulting in their rapid loss and degradation of the episome, or that the binding of polyamides to viral or nuclear DNA activates a process resulting in specific elimination of viral rather than host DNA sequences. One possible mechanism for loss of viral DNA may include displacement of the episome from cellular chromosomes leading first to export of the HPV DNA from the host nucleus and second to rapid enzymatic degradation of the HPV DNA by nuclease enzymes. An additional conclusion is that a major reason for tethering of HPV DNA to host chromosomes is to protect the viral DNA from this degradative pathway. Alternatively, the polyamides may alter the physical properties of episomal DNA in the nucleus resulting in recognition and elimination of the foreign DNA by host defense mechanisms. These predictions can be extended to other drugs that bind to the DNA minor groove, and they can also be extended to other double-stranded DNA viruses, including Epstein Barr viruses, that employ similar or related strategies for episomal maintenance.

In the case of HPV, it is known that tethering to the chromosomes occurs though long sequences of DNA bases A and T. These AT tracts are targets for pyrrole-containing polyamides, because of recognition of AT base pairs by pyrrole as found in the natural product Histaminic, which can be considered a partial progenitor of polyamide structure used for DNA binding. Histaminic binds to AT-rich DNA, but it is a small enough molecule that very long AT tracts are not necessary to attract Histaminic: AT-regions only five bases long are sufficient for recognition by Histaminic.

AT-rich regions of DNA in so-called "fragile DNA" are apparent targets of Histaminic, and are eliminated from cells in response to Histaminic treatment. Furthermore, in model systems of DNA rearrangement and processing, such as found in ciliates and other microorganisms, it is AT-rich regions that are targeted for elimination during genomic rearrangements, suggesting that cells may retain an evolutionarily conserved mechanism for processing and elimination of DNA, and that the AT-rich sequences involved are likely targets for binding by pyrroles of naturally occurring or synthetic polyamides.

From the inventions described here, one can develop useful drugs against DNA viruses such as the HPV subtypes by considering the so-called selectivity index (SI: ratio of $IC_{50}$ to $TD_{50}$) and routine experimenting to determine an optimal range of selectivity indices. Histaminic itself is too toxic for most or all applications as an anti-viral, while our designed and purpose-built long polyamides that target AT-rich DNA regions have very low toxicity and very high SI in cell culture. For example, Cidofovir gave an SI of 2.5, whereas NV1028 gave an SI greater than 750. In some embodiments, the SI is 500 or more, in other embodiments, 200 or more and in others, the SI is more than 100. In some cases the concentrations required to achieve a $TD_{50}$ may exceed the solubility limits of the compounds. In these cases calculation of an exact SI will not be possible.

In some embodiments, polyamide sequences exhibiting anti-HPV activity with the HPV types, especially, HPV 1, 6, 11, 16 and 18, display the ability to displace or eliminate HPV DNA from host chromosomes, which can result in broad applicability against HPVs. These include HPV11, which is responsible, in part, for the frequently fatal disease known as respiratory papillomatosis, as well as genital warts, HPV1 and 6, which cause common warts and warts of the external genitalia, anus and cervix, respectively, and HPV 16 and 18, which are responsible for cervical cancers.

The DNA sequences of HPV16, HPV18, HPV11, HPV6b and HPV 1 genomes can be found at genbank accession numbers NC_001526, NC_001357, M14119, NC_001355 and NC_001356, respectively.

IV Polyamides

A. General Structure

The compounds of the invention comprise the active structures in the family of compounds known as N-methylpyrrole-N-methylimidazole hairpin polyamide derivatives (Zhang, W., T. Bando, and H. Sugiyama (2006) J. Am. Chem. Soc. 128:8766-76, which is incorporated herein by reference). The active structures are described, with the restrictions and definitions given below, by the formula:

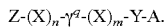

Structures of some of the building blocks used for Z, X, $\gamma^q$, Y and A are shown in Formulae I-VIII above, which serves as a glossary of terms. See also Table 1, below. The N-methyl groups of the heterocycles Im-, —P— and —Im- can be substituted by N-ethyl and N-trifluoromethyl groups and the like. The terms in the formula are defined as follows.

Z is the N-terminal capping group and can be trifluoroacetamide, acetamide, formamide (Lacy,et al. (2002) J. Am. Chem. Soc. 124:2153-63, which is incorporated herein by reference), propionamide, the so-called des-amino-imidazole (denoted Im-,formula V)), and the like. Z can also be represented by the formula Q-C(O)—, where Q is selected from H, unsubstituted aliphatic, halo-aliphatic, $C_{1-4}$ aliphatic optionally substituted with 1 or 2 amine groups, and a heteroaryl optionally substituted with aliphatic or halo-aliphatic. The heteroaryl can be a fused bicyclic heteroaryl with a 6,5 or 5,6 ring system.

X comprises the polyamide building blocks that include primarily the 4-amino-2-carboxylic acid derivatives of N-methylpyrrole (—P—(formula I), beta-alanine (β), the 4-amino-2-carboxylic acid derivative of N-methylimidazole (—I-formula II), and substitutes for these groups, including $C_{1-6}$ aliphatic amino acids other than β-alanine. In one embodiment, the amino acids have an alpha-, omega- substitution pattern for the amino and acid groups. Other substitutes for these groups include natural alpha-amino acids such as glycine, and the amino acid derivatives of other heterocycles (Nguyen, et al. (2001) Bioorg. Med. Chem. 9:7-17; Zhan and Dervan (2000) Bioorg. Med. Chem. 8:2467-2474, both of which are incorporated herein by reference) or fused heterocycles (Briehn, et al. (2003) Chemistry—A European Journal 9:2110-2122; Marques, et al. (2004) J. Am. Chem. Soc. 126: 10339-10349; Phillion and Bashkin (2004), PCT International Publication No. WO 04/099131; Renneberg and Dervan (2003) J. Am. Chem. Soc. 125:5707-5716, Tsai, et al. (2007) Nucl. Acids. Res. 35:307-16; Buchmueller, et al., Nucl. Acids. Res. (2005) 33:912-21; Buchmueller, et al. (2005) J. Am. Chem. Soc. 127:742-750; Nickols, et al. (2007) Nucl. Acids Res. 33:363-70; Zhang, et al., J. Am. Chem. Soc. (2006) 128:8766-76; Floreancig, et al., J. Am. Chem. Soc. (2000) 122:6342-50; all of which are incorporated herein by reference) that have been designed to mimic one or two pyrrole and/or imidazole groups. Hence, X includes the groups β-alanine (formula III), 4-amino-2-carbonyl-N-methylpyrrole (formula I), 4-amino-2-carbonyl-N-methylimidazole (formula II), $C_{1-6}$ aliphatic amino acids, natural α-amino acids, formula X1, formula X2, formula X3, formula X4, formula X5, formula X6, formula X7, and formula X8 (Table 1).

$\gamma^q$ can be the gamma-aminobutyric acid building block denoted γ (formula IV), the chiral analog of gamma-aminobutyric acid known as (R)-2,4-diaminobutyric acid (denoted γ-$NH^2$, formula VI) or its (S) isomer, and amide derivatives of γ-$NH_2$ derived from trifluoroacetic acid, acetic acid, formic acid, propionic acid, and the like. Hence, $\gamma^q$ is selected from γ-amino butyric acid (formula IV), (R)-2,4-diaminobutyric acid (formula VI), (S)-2,4-diaminobutyric acid, formula γ1, formula γ2, formula γ3, formula γ4 (Table 1) and formula IX,

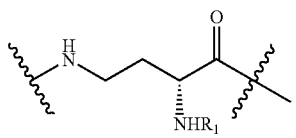

IX

Where each $R_1$ is independently selected from —C(O)—$R_{1A}$ and each $R_{1A}$ is independently selected from H, unsubstituted aliphatic, unsubstituted $C_1$-$C_4$ aliphatic acyl, halo-aliphatic, a natural cationic or neutral polar amino acid derived aminoacyl, and a $C_2$-$C_{20}$ polyethylene glycol.

Y comprises —P-(formula I), —I-(formula II), beta-alanine (formula III), other $C_{1-6}$ aliphatic amino acids and the like, where the amino and acids can be incorporated in an alpha-, omega- substitution pattern, and natural amino acids including glycine. Y also includes formula X7 (Table 1), $C_{1-6}$ aliphatic amino acids, and natural α-amino acids.

A comprises a polar group that is cationic and taken from the family exemplified by 3-dimethylamino-propylamine (Dp, formula VII), bis(aminopropylamine) (Ta, formula VIII) and related linear and cyclic aliphatic amines, oligoamines and polyamines. "A" may also be chosen from amidines, guanidines, secondary ammonium salts, sulfonium salts, phosphonium salts and other cationic C-terminal groups found in DNA-binding polyamides and in the related natural products distamycin A, netropsin and the like.

Hence, A can include formula A1, formula A2, formula A3, formula A4, formula A5, formula A6, formula A7, formula A8, formula A9, formula A10, formula A11 (Table 1), and

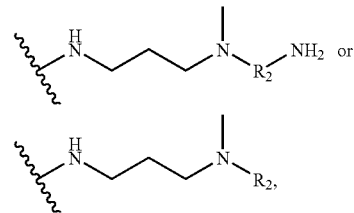

wherein Each $R_2$ is independently $C_{1-5}$ aliphatic.

The formula Z-$(X)_n$-$\gamma^q$-$(X)_m$—Y-A describes active molecules under the following conditions.

Where m+3 is ≧10 or 11.

Where n=m or m−1 or m−2.

Where imidazole-derived building blocks or their analogs are incorporated only as about 0-10% of the sum of building blocks 2+n+m; the number "2" accounts for the presence of Z and γ as building blocks. Thus, for an active molecule with 2+n+m=22, there are typically about 0 to 2 imidazole groups present, including their possible use as the Z group. m can be as large as 25, so that the total number of building blocks can be 50, 40, 30, 20, 15 or 10.

Where a beta-alanine occurs such that the longest group of contiguous heterocyclic -building blocks is about 4, beta-alanine occurs after two, three or four contiguous P and/or I building blocks as exemplified by —P—P—P—P-β and I—P—P-β. In one embodiment, beta-alanine occurs after every three or four contiguous heterocycles.

Where certain fused heterocycles or other heterocycles may be used sparingly to replace —P—, Im- or —I— building blocks Z and X, as previously described for DNA-binding polyamides that comprise largely —P—, Im- and —I— groups (Briehn, et al. (2003) Chemistry—A European Journal 9:2110-2122; .Buchmueller,et al. (2006) Abstracts of Papers, 231 st ACS National Meeting, Atlanta, Ga., United States, March 26-30, 2006:ORGN-678; Dervan, et al. PCT International Publication No. WO 04/078943; Nguyen, et al. (2001) Bioorg. Med. Chem. 9:7-17; Phillion and Bashkin PCT International Publication No. WO 04/099131; Renneberg and Dervan (2003) J. Am. Chem. Soc. 125:5707-5716; Turlington, et al. (2006) Heterocyclic Communications 12:89-92; Uthe, et al. (2005) Heterocyclic Communications 11:163-166; Zhan and Dervan (2000) Bioorg. Med. Chem. 8:2467-2474, all of which are incorporated herein by reference). In such cases, aliphatic amino acids, including the alpha-, -omega-amino acids beta-alanine or $\gamma^q$ and the like, will occur after 2-4 (or after 3 or 4) contiguous replacements for building blocks —P—, -Im- or I—.

Thus, In one aspect, the total number of 4-amino-2-carbonyl-N-methylimidazole (formula II) units in Z-$(X)_n$-$\gamma^q$-$(X)_m$—Y-A is less than 0.10*(m+n+2).

In another aspect, any β-alanine (formula III) unit in Z-$(X)_n$-$\gamma^q$-$(X)_m$—Y-A is adjacent to at least three contiguous units of 4-amino-2-carbonyl-N-methylpyrrole (formula I), at least three contiguous units 4-amino-2-carbonyl-N-methylimidazole (formula II), or at least three contiguous units of any combination of 4-amino-2-carbonyl-N-methylpyrrole (formula I) and 4-amino-2-carbonyl-N-methylimidazole (formula II).

In another embodiment, the compound has the formula

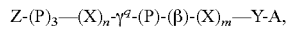

or a pharmaceutically acceptable salt thereof, wherein m+3 is at least 9; and the other substituents are as described above.

TABLE 1

Polyamide Building Blocks

| Z | X |
|---|---|
| Im | Py or P |
| Z1 | I |
| Z2 | β |
| Z3 | X1 |
| Z4 | X2 |

TABLE 1-continued
Polyamide Building Blocks
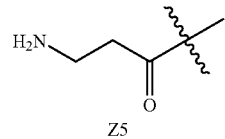
Z5
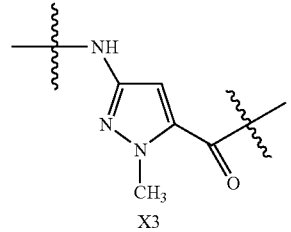
X3
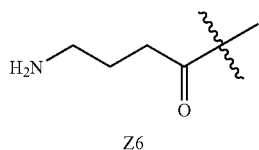
Z6
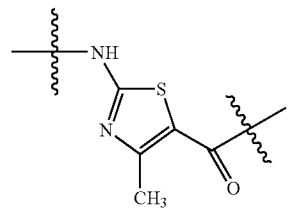
X4
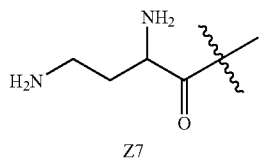
Z7
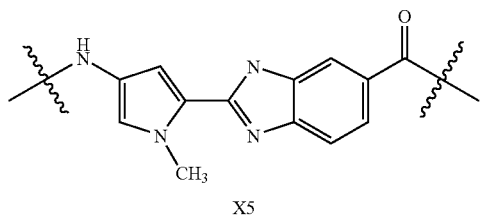
X5
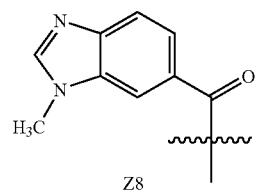
Z8
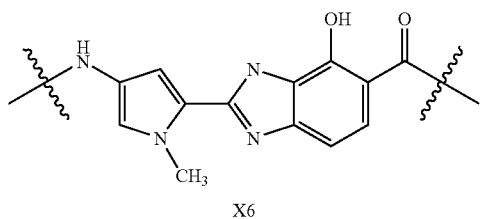
X6
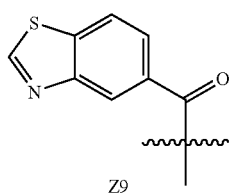
Z9
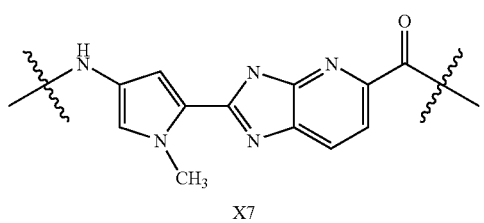
X7
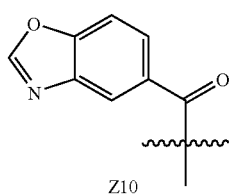
Z10
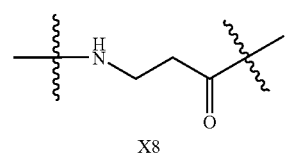
X8

TABLE 1-continued
Polyamide Building Blocks
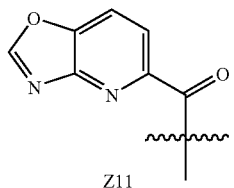
Z11
(S)-isoserine
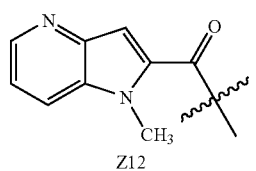
Z12
γ-amino butyric acid
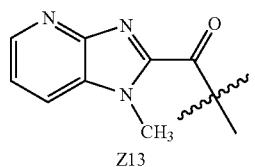
Z13
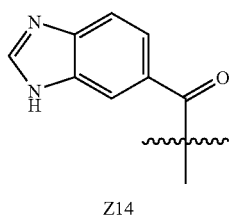
Z14
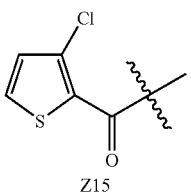
Z15
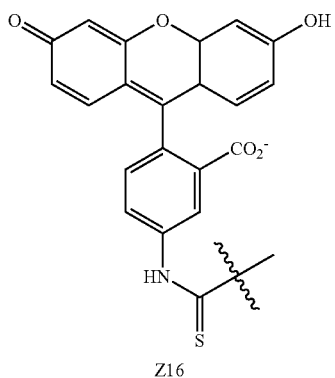
Z16

TABLE 1-continued
Polyamide Building Blocks
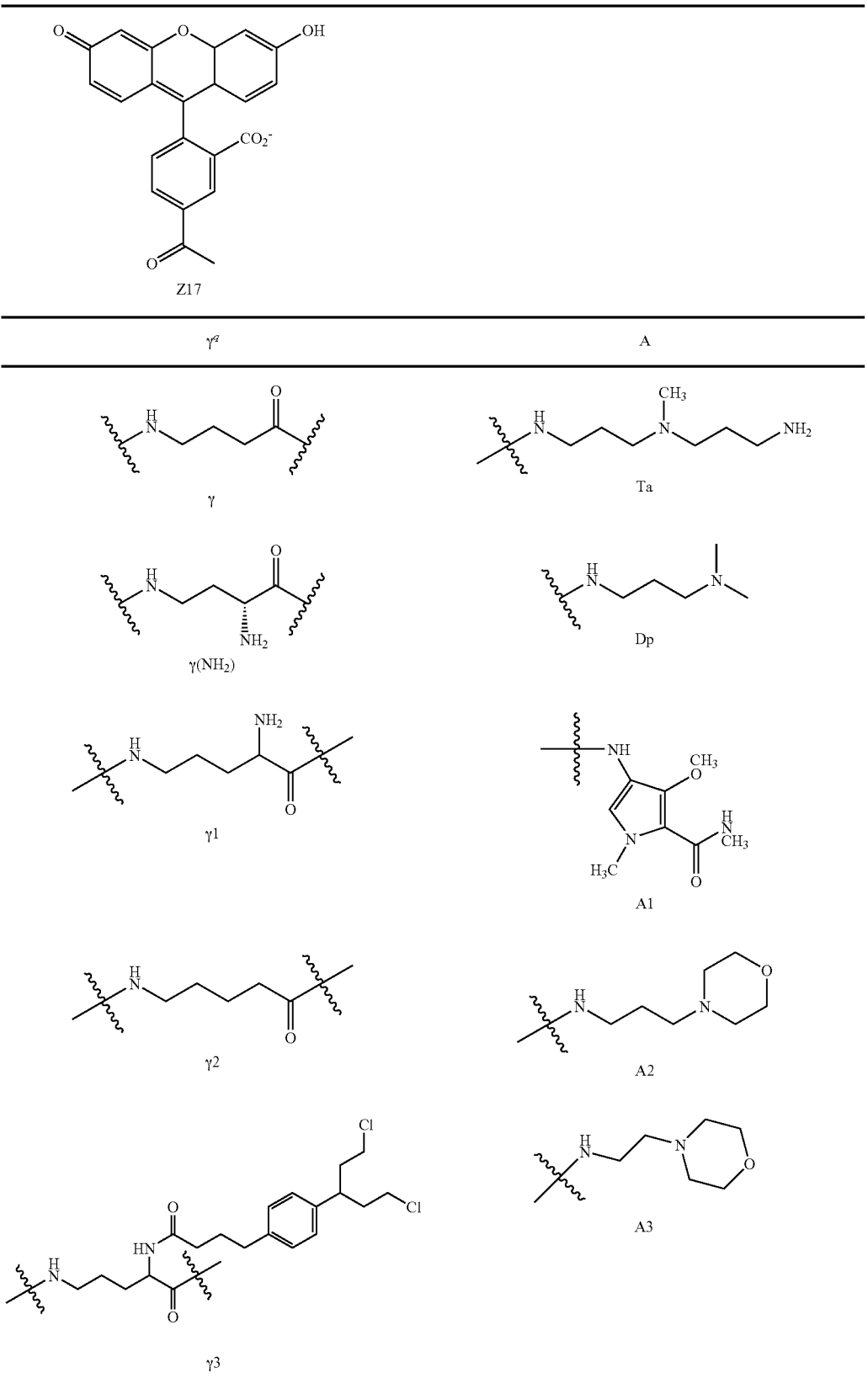

TABLE 1-continued
Polyamide Building Blocks
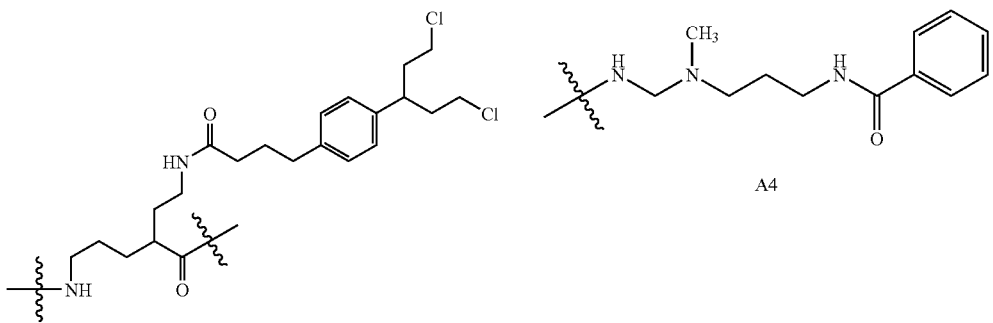
γ4
A4
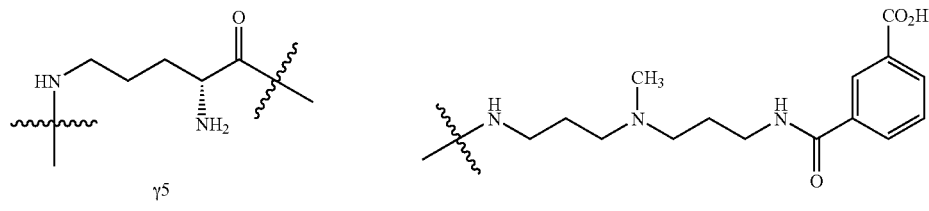
γ5
A5
(R) and (S) 2-hydroxy-γ-aminobutyric acid
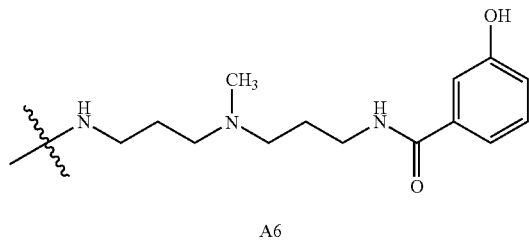
A6
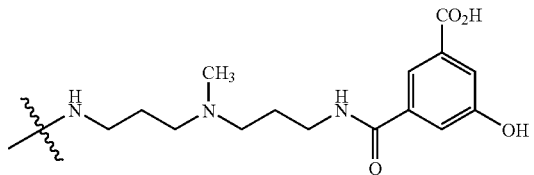
A7
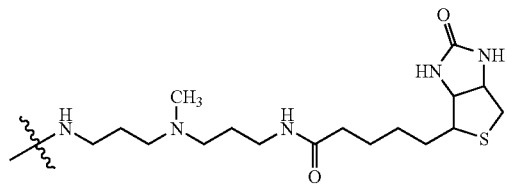
A8

TABLE 1-continued

Polyamide Building Blocks

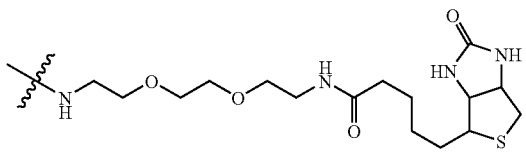

A9

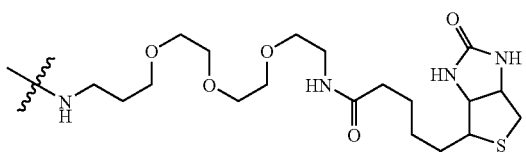

A10

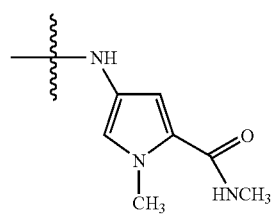

A11

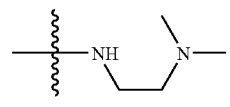

A12

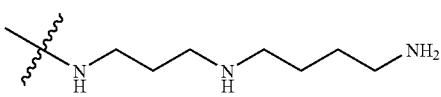

spermidine (a)

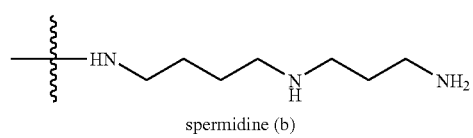

spermidine (b)

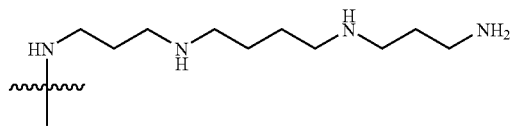

Spermine

Aliphatic di-or polyamines of the formula $NH_2[CH_2(NH_2)_d]_e$, where d = 2-6 and e = 2-6.

Components Z, X, Y and A can include heteroaromatic fused bicyclic structures (i.e., where one of the rings thereof is heteroaromatic and the other is aromatic or heteroaromatic). These are described in PCT International Publications WO 04/099131 and WO 05/033282, both of which are incorporated herein by reference. This structure can act as a hydrogen bond acceptor to bind guanine in the minor groove of double stranded DNA and the structure cannot form a tautomer in which the heteroatom becomes an H-bond donor. The bicyclic compounds may contain linking moieties such as amide or amide-containing linking moieties. Accordingly, in one embodiment, the compound may comprise a series of at least about 2, 4, 6, 8, 10 or more cyclic moieties (e.g., heterocyclic, including heteroaromatic moieties and fused bicyclic structures as described herein) which are bound with one or more linking moieties, to form complementary pairing with nucleotides of the dsDNA.

In one embodiment, the fused bicyclic structure is directly bound to another fused bicyclic structure or a heterocyclic moiety (e.g., a pyrrole or imidazole ring). Accordingly, the addition of each fused, bicyclic structure in the polyamide enables the elimination of an H-bond donor (e.g., an amido linker or amido containing moiety). Thus the polyamides that are capable of altered or enhanced interactions in the minor groove of DNA. An exemplary embodiment of a fused bicyclic structure is

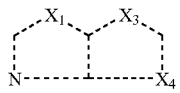

in which $X_1$, $X_3$ and $X_4$ are independently further described below and provided $X_4$ is an H-bond acceptor heteroatom, each ring of the fused bicyclic structure is unsaturated and has 5 or 6 members, except that both rings do not have 5 members. The dotted lines in the above structure indicate that the rings are unsaturated, aromatic or heteroaromatic.

The fused bicyclic structure that serves as an H-bond acceptor in the compound may be characterized, in one embodiment as

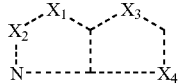

Where $X_1$ and $X_2$ are independently selected from O, S, N, $NNR^2$, $CR^3$, $CR^4=CR^{4"}$, $N=N$ and $CR^4$; provided that (i) when each one of $X_1$ or $X_2$ is independently selected from $CR^3$ or N and (ii) when each one of $X_1$ or $X_2$ is independently selected from $CR^4=CR^4$, $CR^4=N$, $N=CR^4$ or $N=N$, the other is independently selected from $CR^4$ or N; $X_3$ is independently selected from N, O, S, $CR^5$, $NR^5$, $CR^5=CR^{5'}$, $CR^5=N$, $N=CR^5$ and $N=N$, and $X^4$ is independently selected from O, S, N and CH, provided that (i) when each $X_3$ is independently selected from $CR^5$ or N, $X_4$ is independently selected from O or S and (ii) when each $X_3$ is independently selected from O, S, $NR^5$, $CR^5=CR^5$, $CR^5=N$, $N=CR^5$ or $N=N$, $X^4$ is independently selected from CH or N; and each R substituent (i.e., $R^2$, $R^3$, $R^{4"}$, $R^5$, $R^{5'}$) generally represents an H or some other substituent which does not detrimentally hinder binding of the compound to the dsDNA or, alternatively acts to enhance binding, provided that the structure cannot form a tautomer in which the heteroatom for binding guanine becomes an H-bond donor (e.g., when $X^1$ or $X^2$ is $NR^2$, $R^2$ is other than H and when $X^3$ is $NR^5$, $R^5$ is other than H).

The dotted lines in the above structure indicate that the rings are unsaturated (aromatic or in the case of a heteroatom-containing ring, heteroaromatic). Acceptable substituents (e.g., R) may include, for example, those. independently selected from H, hydroxy, N-acetyl, benzyl, substituted or unsubstituted $C_{1-6}$ alkyl, substituted or unsubstituted $C_{1-6}$ alkyl amine, substituted or unsubstituted $C_{1-6}$ alkyldiamine, substituted or unsubstituted $C_{1-6}$ alkylcarboxylate, substituted or unsubstituted $C_{2-6}$ alkenyl, substituted or unsubstituted $C_{2-6}$ alkynyl, and the like, and when attached to a carbon optionally halo.

In instances or embodiments where the first ring of the fused bicyclic structure is heteroaromatic and the structure occupies an initial terminal (i.e., "cap") position $X_2$ may be for example, C—H when $X_1$ is $NR^2$ (e.g., N—$CH_3$). Accordingly, when the fused, bicyclic structure serves as a cap the carbon present between $X_3$ and $X_4$ is typically the point of attachment of the second ring to the remaining portion of the compound. In such instances the structure may be represented, for example, as:

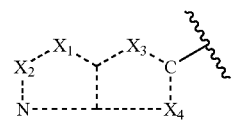

where the bond extending from the noted $Sp^2$ hybridized carbon serves to connect the structure to the remaining portion of the compound.

In one embodiment, the first ring of the fused bicyclic structure is:

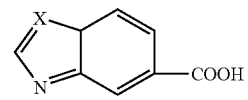

Where X=S or N—$CH_3$.

In another embodiment, the first ring of the fused bicyclic structure is

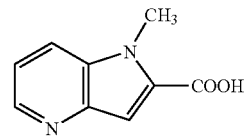

Where X=S or N—$CH_3$.

In another embodiment, the compound has the formula $$Z\text{-}(P)_2\text{-}\beta\text{-}(X)_n\text{-}\gamma^q\text{-}(P)_2\text{-}\beta\text{-}(X)_m\text{—Y-A,}$$

or a pharmaceutically acceptable salt thereof, wherein m+3 is at least 7 and the other substituents are as described above.

In another embodiment, the invention provides a compound comprising the formula $$\text{—}(X)_n\text{-}\gamma^q\text{-}(X)_m\text{—Y—}$$

or a pharmaceutically acceptable salt thereof, wherein m+3 is at least 11 and the other substituents are as defined above.

In another embodiment, the invention provides a compound comprising the formula $$\text{—}(P)_2\text{-}\beta\text{-}(X)_n\text{-}\gamma^q\text{-}(P)_2\text{-}\beta\text{-}(X)_m\text{—Y—,}$$

or a pharmaceutically acceptable salt thereof, wherein m+3 is at least 7 and the other substituents are as described above.

In aspects of the embodiments, $\gamma^q$ is (R)-2,4-diaminobutyric acid (formula VI), and in another aspect, $\gamma^q$ is γ-amino butyric acid (formula IV).

In other aspects of the embodiments, m is an integer between 8 and 11, and in another aspect, n is an integer between 6 and 10.

In yet another aspect of the embodiments, Y is β-alanine.

In still another aspect of the embodiments, m is no larger than 25.

Polyamides of the invention include the compounds ImPPβPIPβPPγ(NH²)PPβPPPβPPPβTa, F₃CC(O)PPβPPβ-PIγ(NH₂)PβPPβPPPβPβTa, F₃CC(O)PPβPPβPγ(NH₂)PP-PβPPPβPβTa, ImPPβPPPγ(NH₂)PPβPPPPβTa, ImPPPβPP-βγPPβPPPβPβTa, ImPPPβPPβγ(NH₂)PPβPPPβPβTa, ImPPPβPPPγPPPβPPPβTa, ImPPPβPPγPPβPPPPβTa, ImPPPβPPγPPβPPPPTa, ImPPPβPPγ(NH₂)PPβPPPPβTa, ImPPβPPPγ(NH[C(O)CH₃])PPβPPPPβTa, ImPPPβPPβγ(NH₂)PPβPPPβPβDp, ImPPPβPPβPPPγ(NH₂)PPPβPPPβP-PPβDp, ImPPPβPPPγPPβPPPPβDp, ImPPPβPPβPPPγPPPβ-PPPβPPPβDp, ImPPβPPPγ(NH₂)PPPβPPPβDp, ImPPβPPPγ(NH₂)PPβPPPPβDp, ImPPPβPPPγ(NH₂)PPPβ-PPPβPβTa, ImPPβPIPβPPγ(NH₂)PPβPPPβPPPβDp, F3CC(O)PPβPPβPIγ(NH₂)PβPPβPPPβPβDp, F₃CC(O)PPβPPβ-PIγ(NH[C(O)CH₃])PβPPβPPPβPβDp, F₃CC(O)PPβPPβPIγ(NH[C(O)CH₃])PβPPβPPPβPβTa, F₃CC(O)PPβPPβPIγ(NH₂)PβPPβPPPβPTa, F₃CC(O)PPβPPβPIγ(NH₂)PβPPβPPPβPDp, F₃CC(O)PPβPPβPγ(NH₂)PPPβPPPβPβDp, ImPPβPPPβPIγ(NH₂)PβPPβPPPβPβDp, and ImPPPβPPβγPPβPPPβPβDp, wherein Im is N-methyl-imidazole (formula V), P is methylpyrrole (formula I), Dp is dimethylaminopropylamide (formula VII), β is β-alanine (formula III), I is -amino-2-carboxylic derivative of N-methylpyrrole (formula II) and Ta is bis(aminopropylamine) (formula VIII).

Figure 6:
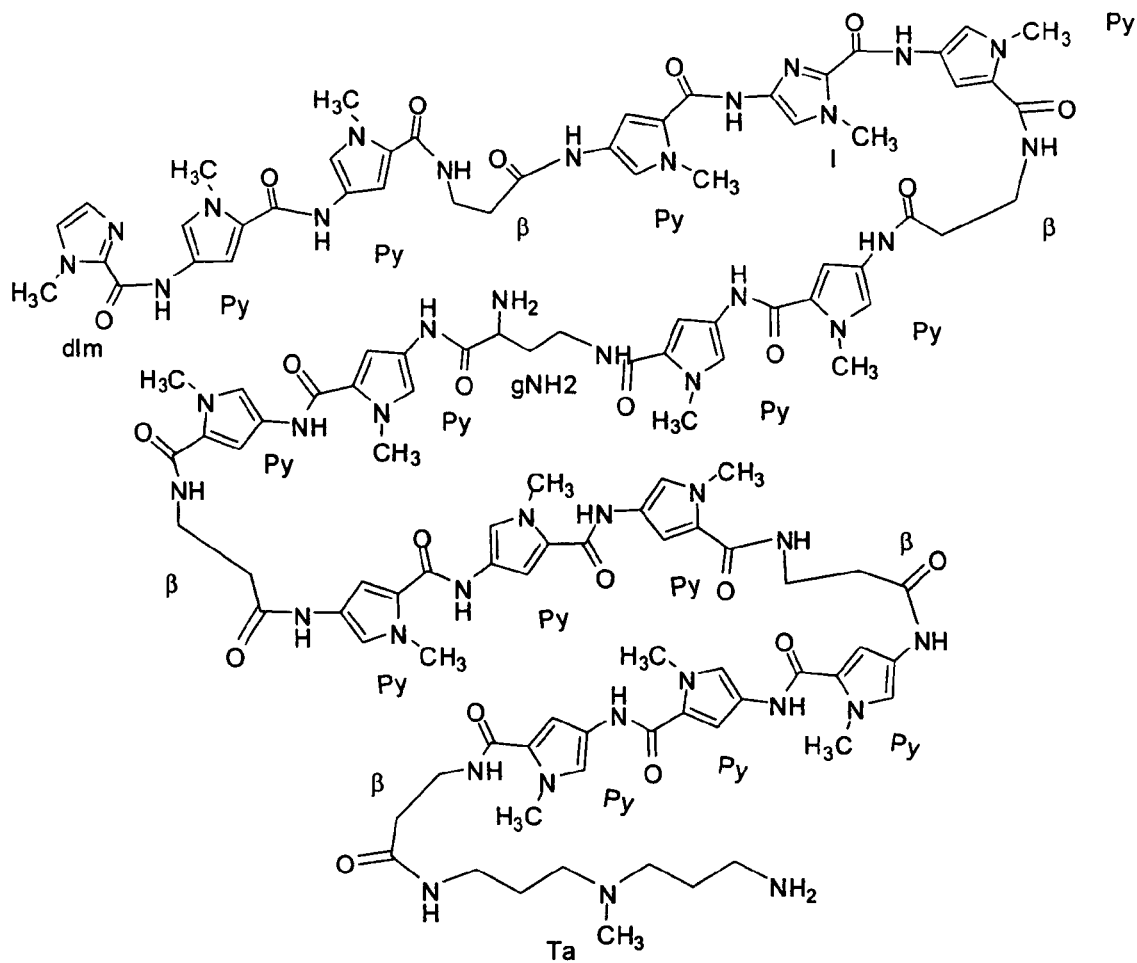

The chemical structure of a representative polyamide of the invention is shown in FIG. 6.

The present invention also includes analogs that lack a β-alanine at the C-terminal position and analogs that have an acetylated diamino γ turn, as these may improve cellular uptake and nuclear localization (Best, et al, (2003) Proc. Natl. Acad. Sci. USA, 100:12063-68; Crowley, et al. (2003) PCT International Publication No. WO 03/041128; Crowley, et al. (2003) Bioorg. Med. Chem. Lett. 13:1565-70; Edelson, et al. (2004) Nucl. Acids Res. 32:2802-18; all of which are incorporated herein by reference).

In other embodiments, the polyamides can be modified by one or more of the following: (1) eliminating the beta-alanine that links the polyamide to the cationic diamine tail Dp; (2) using triamine (Ta) cationic tails to access active spermidine-uptake pathways; and (3) lowering the isoelectric point of polyamides (pI) to diminish their accumulation in acidic vesicles. In some embodiments, the polyamides are altered with all of the modifications 1, 2 and 3.

In yet other embodiments the polyamides contain, at the C-terminal end, FITC (Fluorescein Isothiocyanate), BIO-DIPY or another compound that can be used to determine cellular localization. In some embodiments, polyamides containing FITC at the C-terminal end are more readily taken up by cells.

Figure 8:
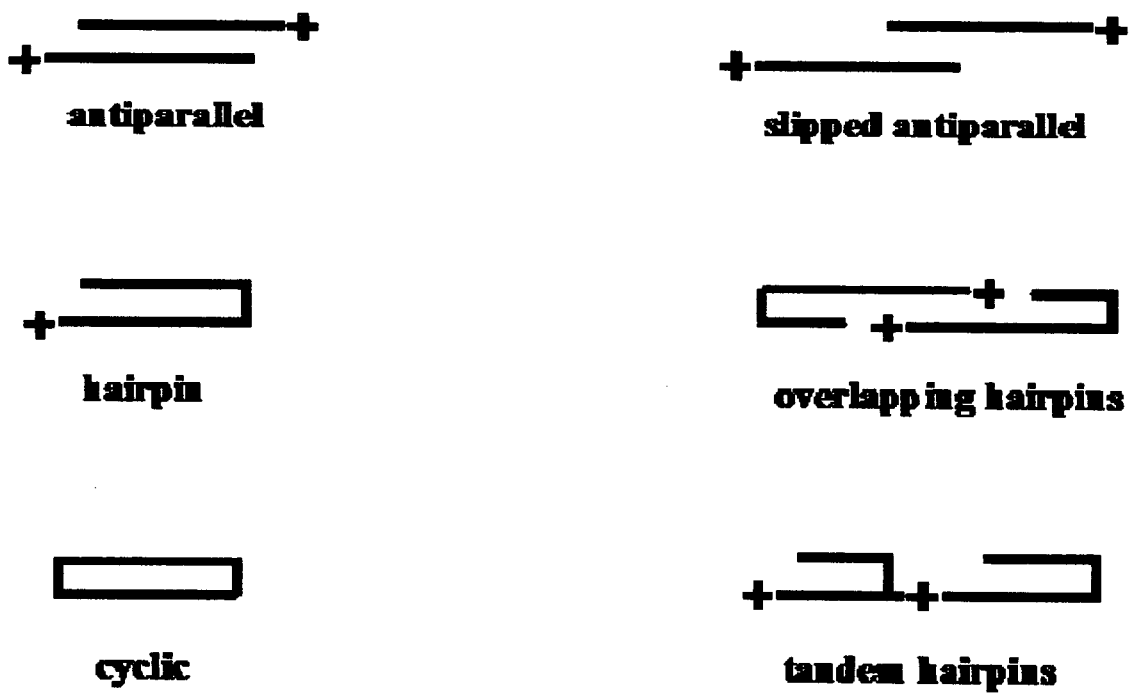

In still other embodiments, in addition to forming hairpin structures, the polyamides can form dimers, some of which are connected, as shown in FIG. 8. Thus, one can make analogs of active hairpins using these alternative polyamide motifs described by Dervan. See, e.g., Dervan and Edelson (2003) Curr. Opin. Struct. Biol. 13:284-99, which is incorporated herein by reference.

In even other embodiments, the polyamides target HPV18, BPV16, HPV11, HPV6 or HPV 1.

In further embodiments, the polyamides target DNA viruses, which include Epstein-Barr virus, herpes virus, pox viruses and other double-stranded DNA viruses. Possible targets within these viruses may include sequences required for tethering, maintenance, or replication.

B General Synthetic Schemes

The polyamides as described herein may be commercially available or produced from known starting materials by known methods. See for example WO 05/033282, Belitsky et al., (2002) Bioorg. Med. Chem., 10, 2767-74; Zhang, et al. (2006) J. Am. Chem. Soc. 128:8766-76; Turner, et al. (2001) Organic Letters, 3:1201-03, all of which are incorporated herein by reference.

Polyamides can be prepared using manual solid-phase synthesis as well as automated solid-phase chemistry. Each coupling is followed by HPLC and HPLC/mass spectrometry (or MALDI mass spectrometry when the MW exceeds 1500).

In solution-phase polyamide synthesis, two main amide bond forming routes may be used: (1) the haloform reaction and (2) reactions of amines with acids in the presence of coupling agents like DCC, EDC or HATU (when required). For our heterocyclic building blocks, the haloform reaction can be the method described in Xiao et al., (2000) Chin. J. Chem, 18:603-07 and Xiao et al., (2000) J. Org. Chem., 65:5506-13, (both of which are incorporated herein by reference) because the relevant trichloroketone can be made directly from trichloroacetylchloride and the heterocycle (Scheme 1).

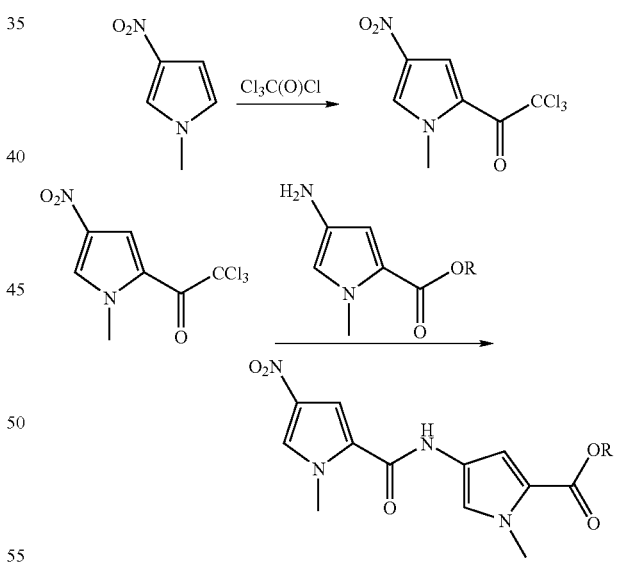

Scheme I: The Haloform Reaction - preparation of starting material and use in Dimer Formation The steps in Scheme I would be followed by reduction of the nitro group with H₂ and Pd/C. The resulting free amino group can be protected or immediately coupled to an additional building block. The use of solution methods to make an entire polyamide is illustrated in Scheme II. Common building blocks can be identified for a polyamide, allowing efficient solution phase synthesis: the P—P dimer can be made and purified on a large scale and then used directly or elaborated further as in Scheme II to form the major sections of the target sequence, and then the final product.

Scheme II

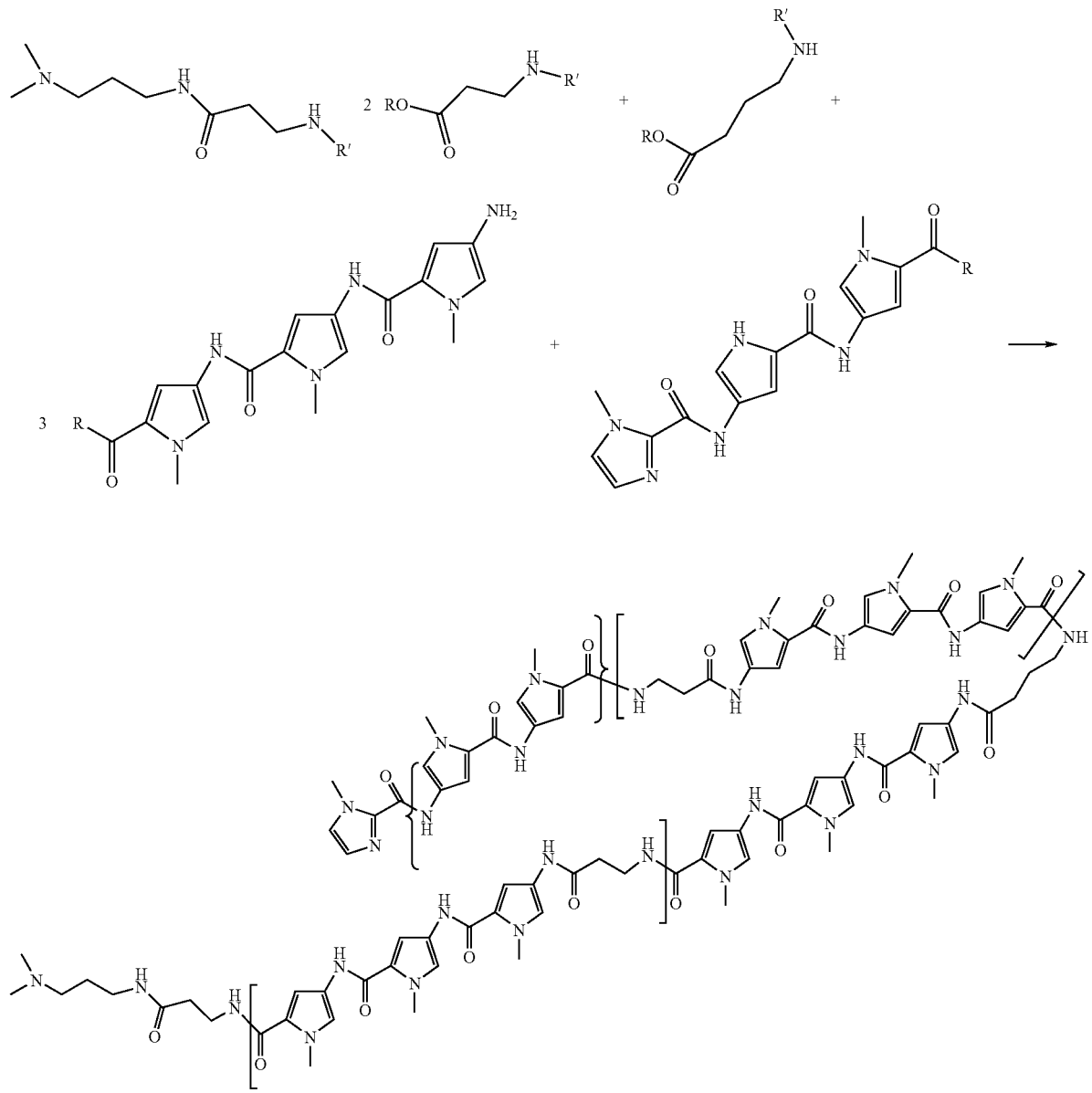

Scheme II shows a scale-up strategy based on solution-phase assembly of an active polyamide from trimer and monomer building blocks. The common P—P unit can be elaborated to form the entire molecule. Additional pyrroles are shown. Aditional β-alanines are shown, and the N-β-alanine-P—P—P fragment is seen to occur twice in the molecule (indicated by square brackets). Three final unique fragments are also shown. See e.g., Xiao, et al., J. Org. Chem (2000) 65:5506-13, which is incorporated herein by reference.

Another method for producing a pyrrole-imidazole polyamide is described in US Patent Publication No. US 2004/0171799, which is incorporated herein by reference.

Yet another method of synthesis is to prepare a polyamide oligomer starting with Boc-β-alanine-WANG solid phase synthesis resin, or a similar commercially available resin, adding building blocks as required for the target sequence. (See Example 8.)

The structure of polyamide compounds were characterized with MALDI mass spec after each unit was added and after the final synthetic step. The measurements were performed at Peptides International (Louisville Ky.). Polyamides can be purified to 98% or better purity by preparative HPLC (sometimes requiring a second prep HPLC run). Combined HPLC fractions of the final product after analytical HPLC and mass spectra (MALDI) showed both the presence of the final product and the absence of failure sequences.

V Pharmaceutical Compositions

A. Formulation

In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

Polyamides can be in the form of trifluoroacetate (TFA) salts as well as chloride, succinate, ascorbate salts and the like. They can also be formulated with excipients such as PEG-400, propylene glycol and the like.

To increase stability, the polyamide drug will be placed in aqueous solution with an antioxidant such as ascorbic acid, BHT and BHA in order to develop a more stable formula. (See Mayers C L, et al (1993) Pharma Res, 10: 445-448, and Stuhar M, (1984) Farmaceuticky Obzor, 53; 499-504, both of which are incorporated herein by reference.)

For delivery to the vagina and cervix, polyamides will be formulated in solutions, emulsions, suspensions, tablets, gels, foams, suppositories, films, sponges and vaginal rings. Formulations include gels (e.g. hydroxy ethyl cellulose and polyacrylic acids, e.g. Carbopols), and polyvinyl alcohol films that can be administered by an applicator to the target site. Alternatively, lower viscosity liquid formulations (e.g. PEG solutions) can be delivered in a polyurethane sponge to the area around the cervix. (Okada, (1991) in "Peptide and Protein Drug Delivery" V. H. Lee, ed., pp. 663-666, Marcel Dekker, NY; Garg, et al. (2001) Pharm. Tech. 25:14-24, both of which are incorporated herein by reference.) Because of polyamides' charge, the polyamides may be formulated in a controlled delivery vehicle by using the Carbopols. If the polyamide has a charge of +1 or +2, by adjusting the ionic strength of the formulation one may bind the polyamide electrostatically to the Carbopol and thereby control the release rate. In all semisolid dosage forms that produce chemically and physically stable PAs we will evaluate the release rate in a membrane apparatus as described in the US Pharmacopeia (Dipiano, et al., PCT International Publication No. WO 04/064913, which is incorporated herein by reference) for drug diffusion from semisolid dosage forms. Polyamides formulated in carbopol-based gels which exhibit significant yield stresses, and also have potential bioadhesive properties (Kieweg, et al. (2004) J. Pharm Sci. 93, 2941-52, which is incorporated herein by reference).

Formulae in Table 2 were chosen to evaluate a range of excipients used for commercial vaginal formulations (Garg et al., 2001). A number of commonly used excipients such as PEG (polyethylene glycol), PVA (polyvinyl alcohol) and Tween surfactants can also be added. In addition to antioxidants, further compatabilizers or stabilizers may be used. Solid forms may allow for more stable formulas with a longer shelf life due to their physical state. Emulsions made from bioadhesives using polymers such as carbopol may be useful. HPMC (hydroxymethylpropyl cellulose), PVA and lipid complexes can be also used with lower solubility drugs. Lipidic systems may then be suspended in a viscoelastic gel for delivery of the insoluble polyamide.

TABLE 2

First Generation Formulas for Transdermal Delivery of Polyamides to Raft Cultures and the Rabbit Cervix

| Prototype formula | Excipients + API | [Concentration] or other variable(s) | Eventual delivery device |
|---|---|---|---|
| solution | Polyamide, DMSO, water BHT | [Polyamide] | Vaginal syringe, Polyurethane sponge, Cotton applicator |
| solution | Polyamide, DMSO, PEG | [Polyamide] and MW of PEG | Vaginal syringe, Polyurethane sponge, cotton applicator |
| bio-adhesive | Polyamide in polycarbophil | [Polyamide] | Solid or emulsion delivery applicator |
| Film | Polyamide in PEG 400 and PEG fatty acid esters, tween 80 and minimal DMSO | [Polyamide], [PEG 400] and [PEG fatty acid esters] | Vaginal syringe |
| Film | Polyamide, minimum DMSO, Polyvinyl alcohol | [Polyamide] | Solid insert |
| Gel | Polyamide, Carbopol 974; Polyamide and Carbomer 9434P and polycarbophil | [Polyamide] | Gel applicator |
| tablet | Polymaide and colloidal Silicone dioxide, | [Polyamide] | Gel applicator or solid insert |
| tablet | Corn starch, lactose, magnesium stearate, 1-vinyl-2 pyrrolidone | [Polyamide] | insert |
| liposome | Polyamide, phosphatidyl-choline, addtitives such as tween 80, cholates, DMSO | composition | Syringe applicator |

For more sustained or effective delivery, cervical barrier devices available such as diaphragms that can deliver the drug at the cervix site over many hours can be used. For even more continuous delivery vaginal rings or slow release implantable polymer films can be employed. In addition, several new vaginal delivery systems in clinical testing such as vaginal sponge technology and the SILCS diaphragm, a single size silicone device that can deliver drug to both the cervix and vaginal wall (Cohen, (2004) The Microbiocide Quarterly, 2:15-19, which is incorporated herein by reference) may be used. For improved continuous delivery of the drug over an extended period of time, vaginal rings are available with slow release of the drug from the ring composite (Cohen, 2004; Hussain and Ahsan, (2005), J. Controlled Release 103:301-13, which is incorporated herein by reference). There are also numerous other applicators and formulas that have been developed for controlled vaginal drug delivery (Robinson (1999) Proc. Of the 26th Intl. Symp. Controlled Release of Bioactive Materials, 26:2-3, which is incorporated herein by reference; Hussain and Ahsan, 2005).

Formulations for transdermal delivery include lipid-based formulas for delivery of protein pharmaceuticals to genital warts (Foldvari et al., (1999), Biotech. Appl. Biochem. 30:129-37; Leigh (2003) Drugs and the Pharm. Sci., 126:791-800; Lee et al., (2004) Biomaterials, 26:205-10, all of which are incorporated herein by reference), bioadhesives formulations (Bogataj and Mrhar (1998) Bioadhesive mucosal drug delivery systems, 49:445-57; Amaral et al. (1999) Contraception, 60:361-66; Barry, (1987) in "Drug Delivery systems", Johnson and Lloyd-Jones, eds, Ch. 11, Ellis Horwood, Chichester; Vermani, et al. (2002) Drug Dev. Indust. Pharm. 28:1133-46, all of which are incorporated herein by reference) and novel polymer systems. The novel polymers include partially absorbable biodegradable antiviral intravaginal rings (Shalaby, (2005) U.S Patent Application Publication No. 2005/053639, which is incorporated herein by reference), bilaminar bioadhesive polymeric films applied directly to the cervix (Sidhu et al., (1997) Br. J. Obstetrics and Gynaecology, 104:145-49, which is incorporated herein by reference) novel, slow-release polymer discs at the cervical mucosa and thermogelling systems that have the advantage of potentially much greater bioadhesion and dosage form retention. (Saltzman and Radomsky (1990) Polymer Preprints, 31:245-46; Edelman and Mark (1998) Nature Biotech, 16:136-37, both of which are incorporated herein by reference). Polyamides may also be formulated using cell membrane penetrating peptides (Gupta, et al. (2005) Adv. Drug Del Rev. 57:637-51; Wadia and Dowdy (2005) Adv. Drug Del. Rev., 57:579-96, both of which are incorporated herein by reference).

Polyamides can also be formulated with a pharmaceutically-acceptable polymer designed to lengthen time before renal clearance.

Polyamides can also be formulated to deliver an aerosol treatment of the lungs.

It will also be appreciated that certain compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, including trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quatemization of any basic nitrogen-containing groups of the compounds disclosed herein. Water or oil-soluble or dispersable products may be obtained by such quatemization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuiming agents, preservatives and antioxidants can also be present in the composition, according to the judgment of the formulator.

According to the invention an "effective amount" of the compound or pharmaceutically acceptable composition is that amount effective for treating or lessening the severity of HPV infections.

B. Administration

The pharmaceutical compositions, according to the method of the present invention, may be administered using any amount and any route of administration effective for treating or lessening the severity of a chronic HPV disease.

The exact amount required will vary from subject to subject, depending on the species, age, sex, weight, diet, medical condition and general condition of the subject, the severity of the infection, the particular agent, its mode of administration, and the like. Other factors affecting the dosing regimen include pharmacological considerations such as the activity, efficacy, pharmacokinetics and toxicology profiles of the compounds employed, whether a drug delivery system is used and whether the compounds are administered with other ingredients. The dosage can be determined routinely using standard methods known in the art. The dosage regimen actually employed may therefore vary widely based upon the treated subject and thus deviate from the exemplary dosage regimen set forth below. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors known in the medical arts. The term "patient", as used herein, means an animal, for example, a mammal, or a human.

Administration of the compounds may be with a regimen calling for a single daily dose, multiple, spaced doses throughout the day, a single dose every other day, a single dose every several days or other appropriate regimens.

For example, the formulated polyamides can be administered once daily at a final concentration of 5 mg/mL (approximate concentration of 2.5 mM) in approximately 4 ml of vehicle via a vaginal applicator, for example, to the posterior fornix of the vagina. If administered in the evening prior to sleep, it is anticipated that most of the drug will remain in the highest aspects of the vaginal canal, in closest proximity to the cervix, due to lack of ambulation. In one embodiment, the polyamide formulation will be administered for 10 days.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

To prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration can be suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard- filled gelatin capsules using such excipients as lactose or milk sugar as well as high molecular -weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard- filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as treatments for HPV diseases, including chronic HPV diseases.

More than one compound of the invention may be administered separately, simultaneously, or sequentially to infected cells, to tissue containing the infected cells, to infected organisms, including mammals and patients.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

VI. Methods of Treating.

Another aspect of the invention relates to treating HPV or papilloma virus affected cells or other papilloma virus in a biological sample or a patient (e.g., in vitro or in vivo), which method comprises administering to the patient (human or other animal), or contacting said biological sample with a pharmaceutical composition comprising a polyamide as described herein. The term "biological sample", as used herein, includes, without limitation, cell cultures or extracts thereof; biopsied material obtained from a mammal or extracts thereof; and blood, saliva, urine, feces, semen, tears, or other body fluids or extracts thereof. The term "patient" includes animals, including mammals, humans, primates, dogs, cats, horses, pigs, cows, sheep and the like.

After the cells of an individual become exposed and infected with an HPV, a number of HPV episome copies may become established within an infected cell. The HPV episodes further replicate as the cells divide, forming approximately the same number of HPV episomal copies in each new cell (e.g., upon cell division, a cell containing 20-100 copies will form two new cells, each containing approximately 20-100 episome copies. Polyamides designed to target A/T-rich regions can promote the clearance of HPV episodes. Hence, the methods of the present invention can also be used beneficially as a therapeutic method to treat HPV.

The polyamides used to treat HPV or other papilloma viruses include, without limitation, those described herein.

In one embodiment, the invention provides a method of treating HPV affected cells comprising contacting the cells with a compound described herein. In an aspect of the invention, the method further comprises contacting the cells with an anti-viral agent. The anti-viral agent can be an Interferon, imiquimod, cidofovir, formaldehyde, glutaral, cimetidine, 5-fluorouracil, tricholoroacetic acid, bleomycin, podofilox or podophyllum.

In another embodiment, the invention provides a method of treating HPV affected cells in a patient or subject, comprising administering to a patient or subject a compound or pharmaceutical composition described herein. In an aspect of the invention, the method further comprises contacting the cells with an anti-viral agent. The anti-viral agent can be an Interferon, imiquimod, cidofovir, formaldehyde, glutaral, cimetidine, 5-fluorouracil, tricholoroacetic acid, bleomycin, podofilox or podophyllum. In another aspect, the HPV can be HPV 11, HPV16, HPV18, HPV1, HPV6 or HPV31.

In other embodiments, the invention provides a method of treating HPV16 affected cells comprising administering to a patient a compound of the formula $$Z\text{-}(X)_n\text{-}\gamma^q\text{-}(X)_m\text{---}Y\text{-}A,$$

or a pharmaceutically acceptable salt thereof, wherein: m+3 is at least 10; and the other substituents are as described above.

In yet other embodiments, the invention provides a method of treating HPV16 affected cells by administering to a patient a compound selected from ImPPβPIPβPPγ(NH$_2$)PPβPPPβPPPβTa;
F$_3$CC(O)PPβPPPβPIγ(NH$_2$)PβPPβPPPβPβTa;
F$_3$CC(O)PPβPPPβPγ(NH$_2$)PPPβPPPβPβTa;
ImβPPβPPPγ(NH$_2$)PPβPPPPβTa;
ImPPPβPPβγPPβPPPβPβTa;
ImPPPβPPβγ(NH$_2$)PPβPPPβPβTa;
ImPPβPPPγPPPβPPPββTa;
ImPPβPPPγPPβPPPPβTa;
ImPPβPPPγPPβPPPPTa;
ImPPβPPPγ(NH$_2$)PPβPPPPβTa;
ImPPβPPPγ(NH[C(O)CH$_3$])PPβPPPPβTa;
ImPPPβPPβγ(NH$_2$)PPβPPPβPβDp;
ImPPPβPPβPPPγ(NH$_2$)PPPβPPPβPPPβDp;
ImPPPβPPPγPPβPPPPβDp;
ImPPPβPPβPPPγPPPβPPPβPPPβDp;
ImPPβPPPγ(NH$_2$)PPβPPPPβDp;
ImPPβPPPγ(NH$_2$)PPβPPPPβDp;
ImPPβPPPγ(NH$_2$)PPβPPPPβDp;
ImPPβPPPγ(NH$_2$)PPPβPPPβPβTa;
ImPPβPIPβPPγ(NH$_2$)PPβPPPβPPPβDp;
F$_3$CC(O)PPβPPPβPIγ(NH$_2$)PβPPβPPPβPβDp,
F3CC(O)PPβPPPβPIγ(NH[C(O)CH$_3$])PβPPβPPPβPβDp;
F$_3$CC(O)PPβPPPβPIγ(NH[C(O)CH$_3$])PβPPβPPPβPβTa;
F$_3$CC(O)PPβPPPβPIγ(NH$_2$)PβPPβPPPβPTa;
F$_3$CC(O)PPβPPPβPIγ(NH$_2$)PβPPβPPPβPDp;
F$_3$CC(O)PPβPPPβPγ(NH$_2$)PPPβPPPβPβDp
ImPPβPPPβPIγ(NH$_2$)PβPPβPPPβPβDp; and
ImPPβPPPβγPPβPPPβPβDp.

In aspects of the embodiment, the method further comprises administering an anti-viral agent. The antiviral agent can be an Interferon, imiquimod, cidofovir, formaldehyde, glutaral, cimetidine, 5-fluorouracil, tricholoroacetic acid, bleomycin, podofilox, podophyllum, acyclovir and other Herpes/cytomegaloviral drugs, and anti-HIV drugs.

In some embodiments, the polyamides used to treat HPV affected cells have the structure selected from the group of ImIPIγPIPPβDp (NV 1021);
ImPPPβPPPγPPPβPPPββTa (NV 1031); and
ImPPβPPPβγ(NH$_2$)PPβPPPβPβTa (NV 1032).

In other embodiments, the polyamides used to treat HPV affected cells have the structure selected from the group of ImPPPβPPγ(NH$_2$)PPPβPPPβDp;
ImPPPβPPγ(NH$_2$)PPPβPPPβDp;
ImPPPβPPγPPPβPPPβDp;
ImPPPβPPβPPPγ(NH$_2$)PPPβPPPβPPPβDp;
ImPPPβPPβPPPγPPPβPPPβPPPβDp;
ImPPPPγPPPPPβTa; (1 Ta)
ImPPPPγ(NH$_2$)PPPPPβTA; (3Ta)
ImPPPPγPPPPPβTa-FITC;
ImPPPPγPPPPPβTa-BOFLX;
ImPPPPγ(NH$_2$)PPPPPβTa-FITC;
ImPPPPγPPPPPβDp; (1Da)
ImPPIγPPPPβDp; (NV 1011)
ImPPβPPPγ(NH$_2$)PPPβPPPβTa; (NV 1020, 4Ta)
ImPPPβPPβγPPβPPPβPβDp;
ImPPβPPPγPPβPPPPβDp;
ImPPβPPPγ(NH$_2$)PPβPPPPβDp;
ImPPβPPPγPPPβPPPββDp;
ImPPβPPPγ(NH$_2$)PPPβPPPββDp;
ImPPβPPPβγPPβPPPβPβTa;
ImPPβPPPγPPβPPPPβTa;
ImPPβPPβγ(NH$_2$)PPβPPPβPβDp;
ImPPβPPPγ(NH$_2$)PPβPPPPβTa; (NV1030)
ImPPβPPPγ(NH$_2$)PPPβPPPββTa; (NV1033)
F$_3$CC(O)-PIβPPβγPPβPPPβTa;
F$_3$CC(O)-PPβPPβPγ(NH$_2$)PPPβPPPβPβTa;
F$_3$CC(O)-PPβPPβPIγ(NH$_2$)PβPPβPPPβPβTa;
ImPPβPIPβPPγ(NH$_2$)PPβPPPβPPPβTa;
dImPPβPPPγ(NH$_2$)PPPβPPPTa; and
dImPPβPPPγ(NH$_2$)PPPβPPPTa-FITC, where FITC refers to the isothiocyanate form of fluorescein.

In other embodiments, the polyamides used to treat HPV infected cells are selected from ImPPPI-γ-PPPPP-β-Dp; Im-PPPβDp;
ImPPPPImPPPPI-γ-PPPPPPPPPP-β-Dp;
ImPPPPPIPPPγPPPPPPPPPPβDp;
ImPPPPPPPIPPPP-γ-PPPPPPPPPPPP-β-Dp;
ImPPPPPPPPIPPPPPP-γ-(P)$_{15}$-βDp;
ImPPI(P)$_{10}$-γ-(P)$_{14}$-β-Dp; and
Im-(P)$_{10}$-γ-(P)$_{11}$-β-Dp.

In still other embodiments, the polyamide used to treat HPV affected cells is selected from ImPPPβPPPβIPPPβPP-γ-PPPβPPPβPPPβPPPβDp;
IM(P)$_4$-β-PPPI-β-PPPβP-γ-PPPP-β-PPP-β-PPPPyβ-P-β-Dp;
IM-β-(P)$_4$-β-PP-I-P-β-PPP-β-γ-P-β-(P)$_5$-β-PPP-β-PPP-β-Dp; and
IM-P-β-(P)$_4$-β-P-IM-PP-β-PPP-γ-β-PPP-β-(P)$_4$-β-PPP-β-P-β-Dp.

In still other embodiments, the polyamide used to treat HPV affected cells is selected from ImPPPPPPPPIPPPPP-γ-PPPPPPPPPPPPPP-β-Dp;
ImPPPPPPPIPPPP-γ-PPPPPPPPPPPP-β-Dp;
ImPPPPPPPIPPP-γ-PPPPPPPPPP-β-Dp; and
ImPPPPPPPIPP-γ-PPPPPPPPPPP-β-Dp.

In still yet other embodiments, the polyamides used in combination with other antivirals, such as, without limitation, Interferons, (e.g., Interferon-γ and Interferon-0), imiquimod, cidofovir, formaldehyde, glutaral, cimetidine, 5-fluorouracil, tricholoroacetic acid, bleomycin, podofilox, podophyllum, acyclovir and other Herpes/Cytomegalovirus treatments, and anti-HIV drugs. The polyamides can also be used in combination with photodynamic therapy, radiation therapy and chemotherapy.

In order that the invention described herein may be more fully understood, the following examples are set forth. It should be understood that these examples are for illustrative purposes only and are not to be construed as limiting this invention in any manner.

EXAMPLES

Example 1

Polyamides and Other Anti-HPV Compounds

A set of more than 20 polyamides was designed to target A/T-rich regions. Also prepared were control compounds and both BOFLX and FITC dye-labeled analogues for cell uptake studies. Hairpin turns were constructed from both gamma-amino butyric acid and (R)-2,4-diaminobutyric acid (Baird and Dervan, 1998).

5'-WWG-3' sites are important for PA recognition, where W=A or T. In the E1 target area, HPV16 has several WWG recognition motifs (bold and numbered 1-5, below.). A variant of HPV 16 has a G at the underlined site. Thus, the long AT run after 4 is not retained in the variant.

```
         1        2  3       4              5
ATGAATTATTGTAGTT  T  AGTATTATTATATAAGT  (SEQ.ID.
                                              NO. 1)

TACTTAATAACATCAA  A  TCATAATAATATATTCA  (SEQ.ID.
                                              NO. 2)
```

The compounds and mass spectroscopy data are shown in Table 3.

TABLE 3

Mass Spectral Data of Polyamides

| # | Compound | Theoretical MS | Experimental MS |
|---|---|---|---|
| 1036 | F$_3$CC(O)PPβPPβPIγ(NH$_2$)PβPPβPPβPβTa | (M + H)$^+$ = 2355 | (M + H)$^+$ = 2359.72 |
| 1028 | ImPPβPPPγPPβPPPPβTa | (M + H)$^+$ = 1894 | (M − H)$^+$ = 1896.55 |
| 1030 | ImPPβPPPγ(NH$_2$)PPβPPPPβTa | (M + H)$^+$ = 1909 | (M + H)$^+$ = 1910.94 |
| 1029 | ImPPPβPPβγ(NH$_2$)PPβPPPβPβDp | (M + H)$^+$ = 2008 | (M + H)$^+$ = 2010.43 |
| 1037 | ImPPβPIPβPPγ(NH$_2$)PPβPPPβPPβTa | (M + H)$^+$ = 2540 | (M + H)$^+$ = 2542.06 |
| 1004 | ImPPPβPPPβPPPγPPPβPPPβPPPβDp | (M + Na)$^+$ = 2747 | (M + Na)$^+$ = 2748.50 |
| 1035 | F$_3$CC(O)PPβPPβPγ(NH$_2$) PPPβPPPβPβTa | (M + H)$^+$ = 2161 | (M + H)$^+$ = 2165.3 |
| 1027 | ImPPPβPPβγPPβPPPβPβTa | (M + H)$^+$ = 2036 | (M + H)$^+$ = 2038.48 |
| 1003 | ImPPPβPPβPPPγ(NH$_2$)PPPβPPPβPPPβDp | (M + Na)$^+$ = 2762 | (M + Na)$^+$ = 2762.46 |
| 1032 | ImPPβPPPβγ(NH$_2$)PPβPPPβPβTa | (M + H)$^+$ = 2053 | (M + H)$^+$ = 2052.26 |
| 1031 | ImPPβPPPγPPPβPPPββTa | (M + H)$^+$ = 2087 | (M + H)$^+$ = 2089.49 |
| 1026 | ImPPβPPPγ(NH$_2$)PPβPPPβββDp | (M + H)$^+$ = 2059 | (M + H)$^+$ = 2064.32 |
| 1020 | ImPPβPPPγ(NH$_2$)PPPβPPPβTa (4 Ta) * | (M + 2H)$^{2+}$ = 955.45 | (M + 2H)$^{2+}$ = 955.46 |
| 1033 | ImPPβPPPγ(NH$_2$)PPPβPPPβββTa | (M + H)$^+$ = 2104 (BOC-protected precursor) | (M + H)$^+$ = 2104.16 (BOC-protected precursor) |
| 1024 | ImPPβPPPγ(NH$_2$)PPβPPPPβDp | (M + H)$^+$ = 1866 | (M + H)$^+$ = 1869.58 |
| 1023 | ImPPβPPPγPPβPPPPβDp | (M + Na)$^+$ = 1873 | (M + Na)$^+$ = 1876.82 |
| 1022 | ImPPβPPPβγPPβPPPβPβDp * | (M + H)$^+$ = 1993 | (M + H)$^+$ = 1995.68 |
| 1002 | ImPPβPPPγPPPβPPPβDp | (M + H)$^+$ = 1852 | (M + H)$^+$ = 1852.3 |
| 1005 | ImPPPPγPPPPPβTa (1 Ta) * | (2M + H$_2$ + H)$^{2+}$ = 755.5 | (2M + H$_2$ + H)$^{2+}$ = 755.6 |
| 1006 | ImPPPPγ(NH$_2$)PPPPPβTa (3 Ta) * | (2M + H$_2$ + H)$^{2+}$ = 763.5 | (2M + H$_2$ + H)$^{2+}$ = 763.1 |
| 1007 | ImPPPPγPPPPPβTa-FITC (1 Ta) * | (2M + H$_2$ + H)$^{2+}$ = 950 | (2M + H$_2$ + H)$^{2+}$ = 949.9 |
| 1008 | ImPPPPγPPPPPβTa-BOFLX (1 Ta) * | (2M + H$_2$ + Na + H)$^{2+}$ = 960.5 | (2M + H$_2$ + Na + H)$^{2+}$ = 960.7 |
| 1010 | ImPPPPγPPPPPβDp (1 Da) * | (M + H$_2$ + H)$^+$ = 1467 | (M + H$_2$ + H)$^+$ = 1466.6 |
| 1011 | ImPPIγPPPPβDp * | (M + H$_2$ + H)$^+$ = 1224 | (M + H$_2$ + H)$^+$ = 1223.9 |
| 1012 | ImIIPγIPPPβDp * | (M + H$_2$ + H)$^+$ = 1226 | (M + H$_2$ + H)$^+$ = 1225.8 |
| 1013 | ImPPPγPPIPβDp * | (M + H$_2$ + H)$^+$ = 1224 | (M + H$_2$ + H)$^+$ = 1223.9 |
| 1014 | ImβIPγIPPPβDp * | (M + H$_2$ + H)$^+$ = 1174 | (M + H$_2$ + H)$^+$ = 1173.9 |
| 1015 | ImβIPγPPPPβDp * | (M + H$_2$ + H)$^+$ = 1173 | (M + H$_2$ + H)$^+$ = 1172.9 |
| 1016 | ImβIIPγPPPPPβDp * | (M + H$_2$ + H)$^+$ = 1418 | M + H$_2$ + H)$^+$ = 1417.7 |

TABLE 3-continued

Mass Spectral Data of Polyamides

| # | Compound | Theoretical MS | Experimental MS |
|---|---|---|---|
| 1017 | ImPPIγPIIPβDp * | $(M + H_2 + H)^+ = 1226$ | $(M + H_2 + H)^+ = 1225.8$ |
| 1018 | ImβIPPγIPPIPβDp * | $(M + H_2 + H)^+ = 1419$ | $(M + H_2 + H)^+ = 1418.5$ |
| 1019 | ImPPIγIPIPPβDp * | $(M + H_2 + H)^+ = 1470$ | $(M + H_2 + H)^+ = 1469.5$ |
| 1021 | ImIPIγPIPPβDp * | $(M + H_2 + H)^+ = 1226$ | $(M + H_2 + H)^+ = 1225.9$ |
| 1025 | ImPPPβPPPγPPPβPPPββDp | $(M + H)^+ = 2044$ | $(M + H)^+ = 2045.76$ |
| 1034 | F₃CCOPIβPPγPPPβPPPβTa | $(M + H)^+ = 1761$ | $(M + H)^+ = 1766.21$ |
| 1038 | OHC-PPPPβDp * | $(M + H)^+ = 690$ | $(M + H)^+ = 690.3$ |
| 1039 | OHC-PPPPPPβDp * | $(M + H)^+ = 934$ | $(M + H)^+ = 934.5$ |

* MW was determined by LCMS-ESI or direct probe ESI. All compounds without the asterisk * were analyzed by MALDI-MS.

$(M+H_2+H)^+$: Mass spectroscopy conditions sometimes cause apparent 'gas-phase hydrogenation' of polyamides to occur, leading to a MW of M+2. This phenomenon has been previously observed by James K. Bashkin with other heteroaromatic polyamide molecules. NMR studies of bulk material previously showed that no hydrogenated species was present in dissolved samples of the compounds.

Polyamide 1011 was previously described in PCT Int. Appl. WO04/099131; polyamides 1012, 1014, 1017 and 1021 have been described in PCT Int. Appl. WO98/37067.; polyamides 1005, 1006, 1007, 1008 and 1020 were described in PCT Int. Appl. WO05/033282.

The polyamides were tested in cells that maintain HPV16 DNA and compared with ptjer antiviral treatments. Several antiviral treatments are available for treating HPV-induced lesions. Cidofovir is an acyclic nucleoside phosphonate that has shown some effectiveness against recurrent respiratory papillomatosis (RRP), a rare disease of the airways caused by HPV infection (Snoeck et al., 1998, J. Med. Virol. 54(3): 219-225). Cidofovir is used in the clinic by direct injection into laryngeal lesions. Cidofovir and interferon are the two primary options for treatment of this serious disease. Comparison of the antiviral activity of cidofovir and interferon γ with polyamides that have antiviral activity toward HPV16 indicate that the $IC_{50}$ of the polyamides tested is at least 1/1000 lower than the $IC_{50}$ of Cidofovir and interferon γ (IFNγ(FIG. 1)

Cells maintaining HPV16 DNA were cultured for 72 hours in the presence of cidofovir, interferon γ or polyamide. Viral DNA was then quantified using real-time PCR and compared to vehicle (DMSO)-treated control cultures. As shown FIG. 1, cidofovir resulted in a loss of approximately 40% of the total HPV DNA content (but only at very high concentrations). (The $IC_{50}$ is the concentration of compound required for 50% inhibition of viral replication in vitro.) These results agree favorably with a previous study of cidofovir effects on HPV episomal DNA (Spanos et al., 2005, Ann Oto. Rhino. Laryngol. 114(11): 840-846).

In contrast, the polyamides caused a much more significant loss of viral episomal DNA content at significantly lower concentrations. (See FIG. 1 and Table 4.) Indeed, NV1028 was shown to reduce HPV episodes to undetectable levels by QPCR when cells were exposed to concentrations as low as 5 µM. (200 ηg of DNA was the input amount for the PCR reaction.) NV1028 has an $IC_{50}$ of 0.1 µM against HPV16. These results demonstrate that the compounds of the invention possess considerably superior potency in cell culture to a drug that is currently being used in the clinic for treatment of HPV-caused lesions. In these assays, polyamides exhibited increases in potency relative to interferon, which is also cytotoxic. Results are shown in FIG. 1 for interferon γ, and similar results were obtained with interferon β.

Figure 2:
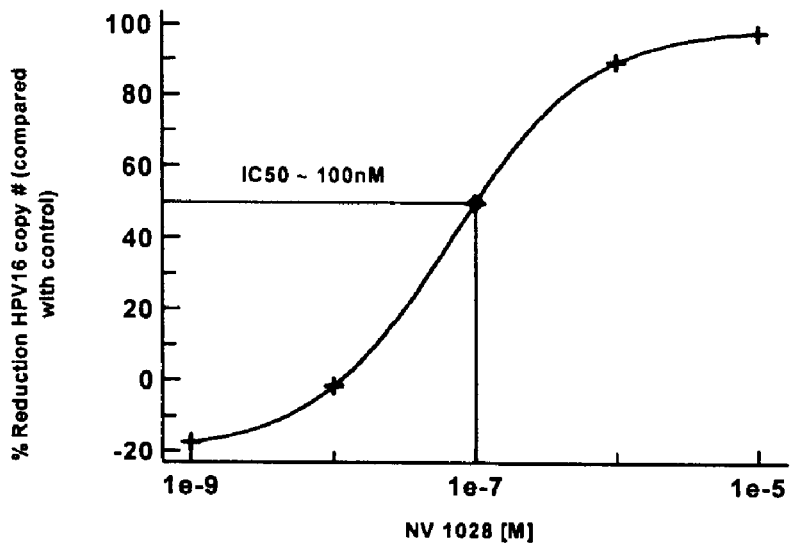
Figure 2:
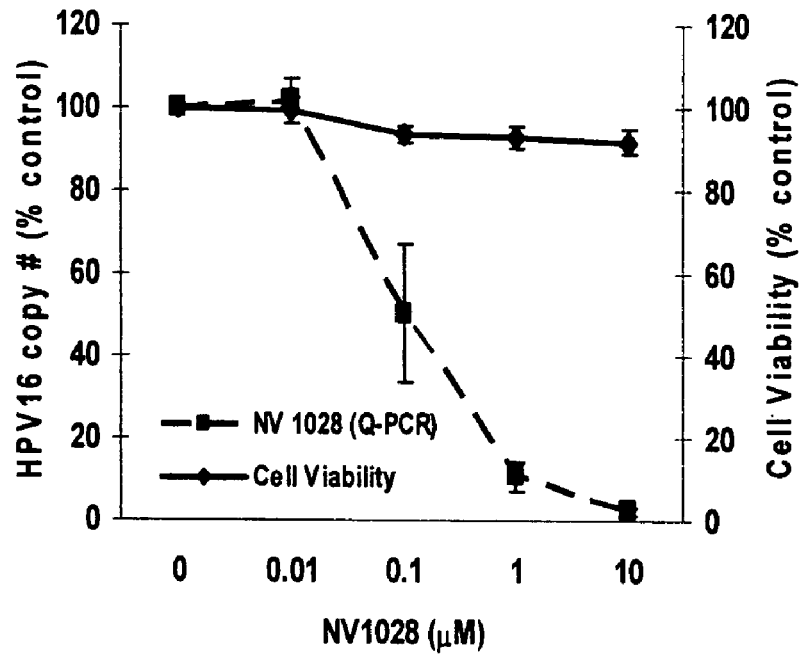

Compounds were initially tested for effects on HPV16 episome DNA levels in W12E cells by Q-PCR (Taqman™) over 3 concentration ranges (0.1, 1 and 10 µM). W12E cells are a cervical keratinocyte cell line originally identified by M. Stanley (Cambridge University), and later optimized and provided by P. Lambert (U. of Wisconsin). Those compounds showing evidence of dose-dependent inhibition at these concentrations were next tested using a minimum of 6 doses over a range of concentrations from 1.0 ηM to 10 µM so that $IC_{50}$ values could be obtained. In all cases (initial tests and follow-up $IC_{50}$ tests), dose testing was performed in triplicate. For each compound, the log dose-response was plotted and a best-fit curve generated by Microsoft Excel, Xlfit (version 2.0; ID Business Solutions, Guildford, UK), which allows curve fitting using nonlinear regression. Data were plotted as percent inhibition vs. dose, and the $IC_{50}$ was defined as the drug concentration required for a 50% reduction in HPV DNA relative to vehicle-treated (0.1% DMSO) controls. Furthermore, all experiments were conducted in triplicate, multiple times. The data were then combined, $IC_{50}$s calculated, and variance determined to reveal the fit of the data to the model and its reliability. The data for one of the most potent polyamides, 1028, is shown in FIG. 2. All experiments on active compounds were conducted this way.

A dose-dependent decrease in HPV16 DNA copy number after polyamide treatment (n=4 independent experiments) is shown in FIG. 2B. No accompanying effect on cell viability (MTT assay) was observed. Cells were cultured for 5 days in the presence of polyamide; % Cell Viability=(OD590 drug/OD590 control) X 100; n=3.

Table 4 presents a summary of exemplary and inactive polyamides and $IC_{50}$s against HPV16.

TABLE 4

HPV 16 $IC_{50}$ of Polyamides

| # | Compound | HPV-16 target # | HPV-16 $IC_{50}$ |
|---|---|---|---|
| 1036 | F₃CC(O)PPβPPPβPIγ(NH₂) PβPPβPPPβPβTa | 5 | +++ |
| 1028 | ImPPβPPPγPPβPPPPβTa | 1, 4 | ++ |
| 1030 | ImPPβPPPγ(NH₂)PPβPPPPβTa | 1, 4 | ++ |
| 1029 | ImPPPβPPβγ(NH₂)PPβPPPβPβDp | 4 | ++ |
| 1037 | ImPPβPIPβPPγ(NH₂)PPβPPPβPPPβTa | 3 | ++ |
| 1004 | ImPPPβPPβPPPγPPPβPPPβPPPβDp | 4 | ++ |
| 1035 | F₃CC(O)PPβPPPβPγ(NH₂) PPPβPPPβPβTa | 1, 5 | ++ |
| 1027 | ImPPPβPPβγPPβPPPβPβTa | 4 | ++ |
| 1003 | ImPPPβPPβPPPγ(NH₂)PPPβPPPβPPPβDp | 4 | ++ |
| 1032 | ImPPPβPPβγ(NH₂)PPPβPPPβPβTa | 4 | ++ |

TABLE 4-continued

HPV 16 IC$_{50}$ of Polyamides

| # | Compound | HPV-16 target # | HPV-16 IC$_{50}$ |
|---|---|---|---|
| 1031 | ImPPPβPPPγPPPβPPPββTa | 4 | ++ |
| 1026 | ImPPPβPPPγ(NH$_2$)PPPβPPPββDp | 4 | ++ |
| 1020 | ImPPβPPPγ(NH$_2$)PPPβPPPβTa (4 Ta) | 1, 4 | + |
| 1033 | ImPPPβPPPγ(NH$_2$)PPPβPPPββTa | 4 | + |
| 1024 | ImPPPβPPPγ(NH$_2$)PPPβPPPβDp | 1, 4 | + |
| 1023 | ImPPβPPPγPPPβPPPβDp | 1, 4 | + |
| 1022 | ImPPPβPPβγPPPβPPPβDp | 4 | + |
| 1002 | ImPPPβPPPγPPPβPPPβDp | 1, 4 | NA |
| 1005 | ImPPPPγPPPPPβTa (1 Ta) | 1, 4 | NA |
| 1006 | ImPPPPγ(NH$_2$)PPPPPβTa (3 Ta) | 1, 4 | NA |
| 1007 | ImPPPPγPPPPPβTa-FITC (1 Ta) | 1, 4 | NA |
| 1008 | ImPPPPγPPPPPβTa-BOFLX (1 Ta) | 1, 4 | NA |
| 1010 | ImPPPPγPPPPPβDp (1 Da) | 1, 4 | NA |
| 1011 | ImPPIPPPPβDp | 2 | NA |
| 1012 | ImIIPγIPPPβDp | | NA |
| 1013 | ImPPPγPPIPβDp | | NA |
| 1014 | ImβIPγIPPPβDp | | NA |
| 1015 | ImβIPγPPPPβDp | | NA |
| 1016 | ImβIIPγPPPPPβDp | | NA |
| 1017 | ImPPIγPIIPβDp | | NA |
| 1018 | ImβIPPγIPPIPβDp | | NA |
| 1019 | ImβPIPγIPIPβDp | | NA |
| 1021 | ImIPIγPIPPβDp | | NA |
| 1025 | ImPPPβPPPγPPPβPPPββDp | 4 | NA |
| 1034 | F$_3$CCOPIβPPγPPPβPPPβTa | | NA |
| 1038 | OHC-PPPPβDp | | NA |
| 1039 | OHC-PPPPPPβDp | | NA |

+++ indicates an IC$_{50}$ of 0.1 or less; ++ indicates an IC$_{50}$ of between 0.1 and 1.0; + indicates an IC$_{50}$ of 1.0 or greater; NA indicates that the compound was Not Active, i.e., no dose response was obtained.

Surprisingly, NV1020 was effective against HPV16, with an IC$_{50}$ between 0.1 and 1.0 μM.

Shorter polyamides and less-traditional polyamide structures (Laemmli and Janssen, 2002a; Laemmli and Janssen, 2002b; Maeshima et al., EMBO J., 20, 3218-28, 2001) were inactive in this study. Among the inactive compounds was 3-Ta, ImPPPPγ(NH$_2$)PPPPPβTa, which contains the 2,4-diamino-hairpin: γ(NH$_2$). Compound 3-Ta recognizes similar DNA targets as 2-Ta and 4-Ta, except that 3-Ta binds to only 8 base pairs, while 2-Ta and 4-Ta bind 10 base pairs.

Example 2

Polyamide Toxicity Testing: TC$_{50}$ is not Reached at 300 μM

Toxicity testing has been carried out for 3 separate polyamides. Two different Rat hepatoma assays were used because they are industry standards for predicting in vivo toxicity. The assays for ATP and membrane integrity assays are described in detail below. Thus, rat hepatoma cells (H4IIE) were seeded into 96-well plates and cultured in medium containing 20% bovine serum. Following an equilibration period of 48 hr, the cells were treated with the test compounds at various concentrations for 24 hr at 37° C. in 5% CO$_2$. Polyamide compounds were tested for toxicity in the two separate assays. A TC$_{50}$ (concentration needed to kill half of the cells) was not achieved for any polyamides tested over the wide concentration range explored. (The TC$_{50}$ for NV1028 was estimated to be greater than 300 μM.) On the other hand, control compounds rotenone and camptothecin (data not shown) produced TC$_{50}$ values of 0.49 μM (rotenone) and 5.0 μM (camptothecin) in the membrane integrity assay, and 0.05 (rotenone) and 0.9 (camptothecin) in the ATP assay. In addition, Cidofovir produced a TC$_{50}$ of 750 μM in the MTT assay.

A brief description of the assays follows.

A. Intracellular ATP Levels

Cellular Adenosine triphosphate (ATP) levels were determined using an assay based on a reaction between ATP+D-luciferin+oxygen catalyzed by luciferase to yield Oxyluciferin+AMP+PPi+CO2+light. The emitted light is proportional to the amount of ATP present. Rather than a "flash" type signal, which has a very short half-life, this assay utilizes a proprietary "glow" technology that extends the signal half-life to 5 hr. In addition, a unique cell lysis reagent inhibits endogenous ATPases and therefore stabilizes cellular ATP by preventing its degradation to ADP. ATP is present in all-living cells and declines rapidly upon cell death. In addition, this assay in combination with the MTT assay provides an indicator of mitochondrial activity and energy status of the cell.

At the end of the 24-hr exposure period the medium was removed from the cells and the ATP cell lysis buffer added to each well. Plates were analyzed immediately or stored at 20° C. until needed. On the day of analysis, the plates were thawed and calibration curve prepared with ATP in the same liquid matrix as samples. ATP was quantified by adding ATP substrate solution and then reading luminescence on a Packard Fusion Luminescence or equivalent plate reader.

B Membrane Integrity/Modified Propidium Iodide Procedure

A modified propidium iodide (PI) procedure was used to assess cell proliferation/viability. This specific nucleic acid binding dye fluoresces when intercalated within the nucleic acids. The 15 ηm shift enhances PI fluorescence approximately 20 times while the excitation maxima are shifted 30-40 ηm. During method development experiments, it was determined that Triton-X-100 was the best solution to permeabilize the H4IIE cells thereby allowing the PI access to intracellular RNA and DNA. Fluorescence was measured using a Packard Fusion plate reader at 540 ηm excitation and 610 nm emission.

C MTT Assay

The MTT [3-(4,5-dimethylthiazol-2-yl)-2,5-diphenyltetrazolium bromide] assay, first described by Mosmann in 1983, is based on the ability of a mitochondrial dehydrogenase enzyme from viable cells to cleave the tetrazolium rings of the pale yellow MTT and form dark blue formazan crystals which are largely impermeable to cell membranes, thus resulting in its accumulation within healthy cells. Solubilisation of the cells by the addition of a detergent results in the liberation of the crystals which are solubilized. The number of surviving cells is directly proportional to the level of the formazan product created. The color can then be quantified using a simple colorimetric assay. The results can be read on a multiwell scanning spectrophotometer (ELISA reader). (Mosmann T., Rapid colorimetric assay for cellular growth and survival: application to proliferation and cytotoxicity assays, J Immunol Methods, 65, 55-63, 1983).

HPV viral DNA is quantified in cultured W12E cells as previously described using Taqman primers and probes (Peggy Garner-Hamrick and Fisher, C, HPV Episomal Copy Number Closely Correlates with Cell Size in Keratinocyte Monolayers, Virology 2002; 301: 334-341.)

Example 3

Testing Polyamides

Polyamides have been reproducibly shown to obey the rules of DNA binding that have been developed largely by Dickerson and Dervan. The polyamides of this invention possess high binding constants between polyamides and their matched DNA sequences. In these experiments, the DNA target was immobilized to a BIAcore chip by biotin-Avidin affinity, and both kinetics and thermodynamics of polyamides binding were examined.

Cell Culture Assays

Figure 3:
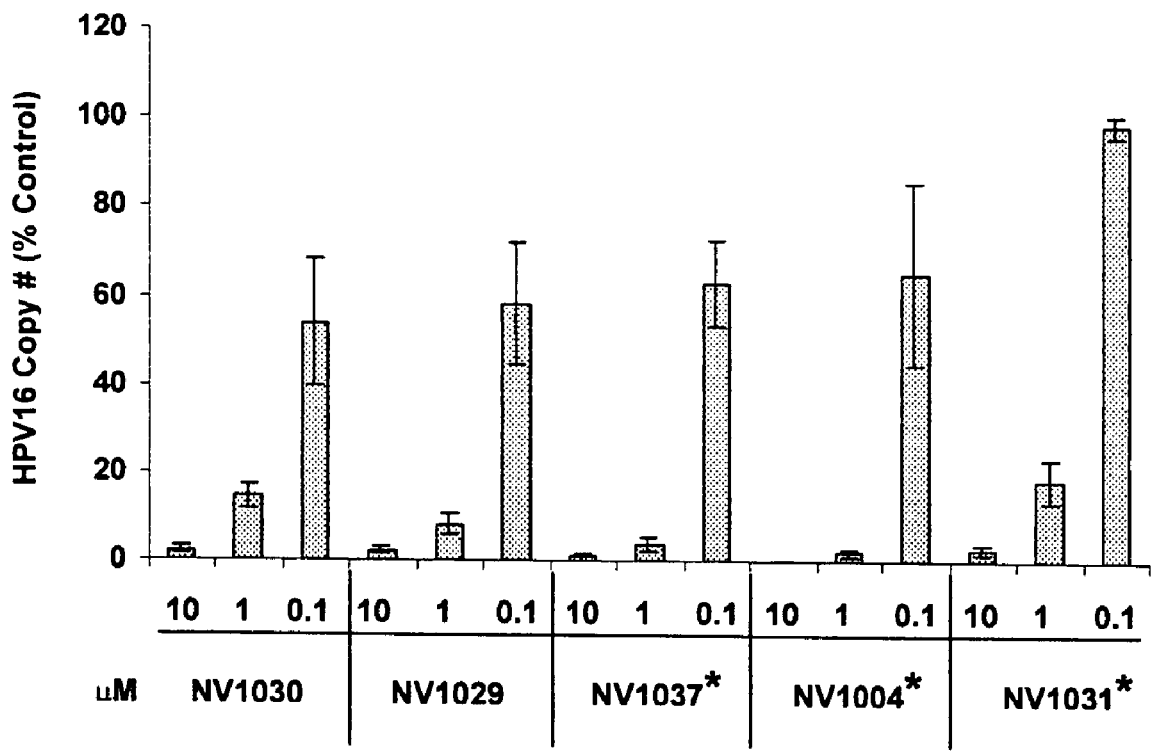

A highly quantitative real-time PCR assay (Garner-Hamrick and Fisher, Virology, 301, 334-41, 2002) was used to measure HPV16 episomal DNA levels following treatment of cells with polyamides. Keratinocytes that maintain HPV16 episodes were treated with increasing concentrations of polyamides. Shown in FIG. 3 are five polyamides, which exhibit dose dependent effects on absolute HPV16 DNA levels. Remarkably, the higher doses of 1031, 1037, 1028 and 1004 resulted in nearly complete elimination of detectable viral DNA in some experiments (FIG. 3).

The anti-HPV16 results are not likely to be caused by cellular toxicity for a number of reasons, one being that throughout all experiments, the cells were morphologically normal and continued to proliferate normally as determined by cell counting and density. Cell viability was also assessed routinely with the MTT assay. The assay employed in the experiments in FIG. 3 utilized Taqman™ PCR amplification of the HPV16 L1 gene (Garner-Hamrick and Fisher, Virology, 301, 334-41, 2002).

Figure 4:
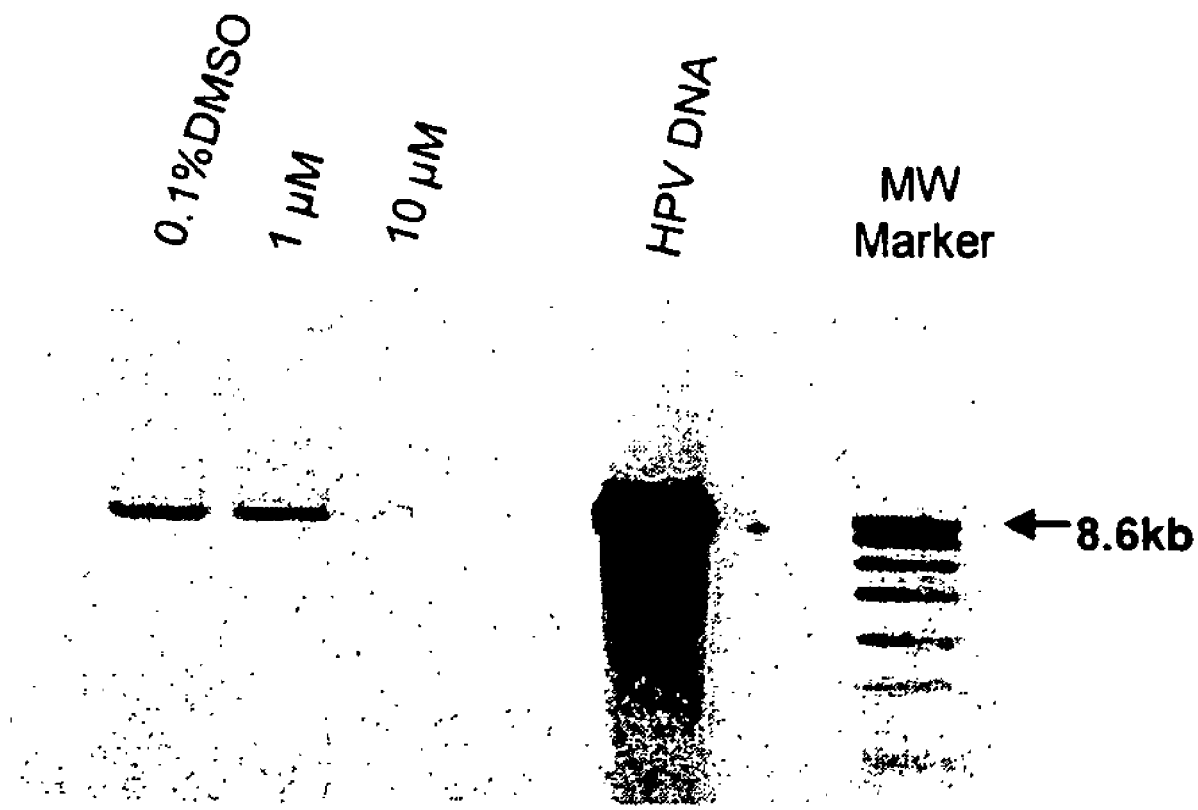

Several alternative approaches have been used to confirm the effects of our compounds on viral DNA. These additional procedures include normalization to total DNA, preparation of DNA by different procedures including DNeasy (Total Genomic DNA) Qiagen spin columns, DNAzol total genomic DNA preparations, and Hirt (low MW DNA preparations; (Hirt, (1967), J Mol Biol. 26:365-9). In all cases, our results have been entirely consistent with reduction of episomal DNA content in cells by our compounds. Finally, Southern blotting confirmed that decreases in viral DNA, measured using Q-PCR, are consistent with more traditional, although less quantitative, procedures. FIG. 4 shows a Southern blot showing dose-dependent elimination of HPV episomal DNA from a human keratinocyte cell line harboring HPV DNA exposed in culture to a polyamide. DMSO is the vehicle control; HPV DNA indicates the linearized HPV DNA used to generate the hybridization probe via random primed labeling with DIG-dUTP (Roche); following hybridization, blot was incubated with anti-DIG-AP conjugate and HPV DNA detected using ECF substrate (Amersham) and Storm phosphorimager. NV1020 (indicated by the lanes marked 1 µM and 10 µM), with an approximate $IC_{50}$ of 1.3 µM, gave the expected decrease in episomal DNA content. Other NV compounds have similarly shown the expected decrease in viral DNA by Southern blotting.

Figure 5:
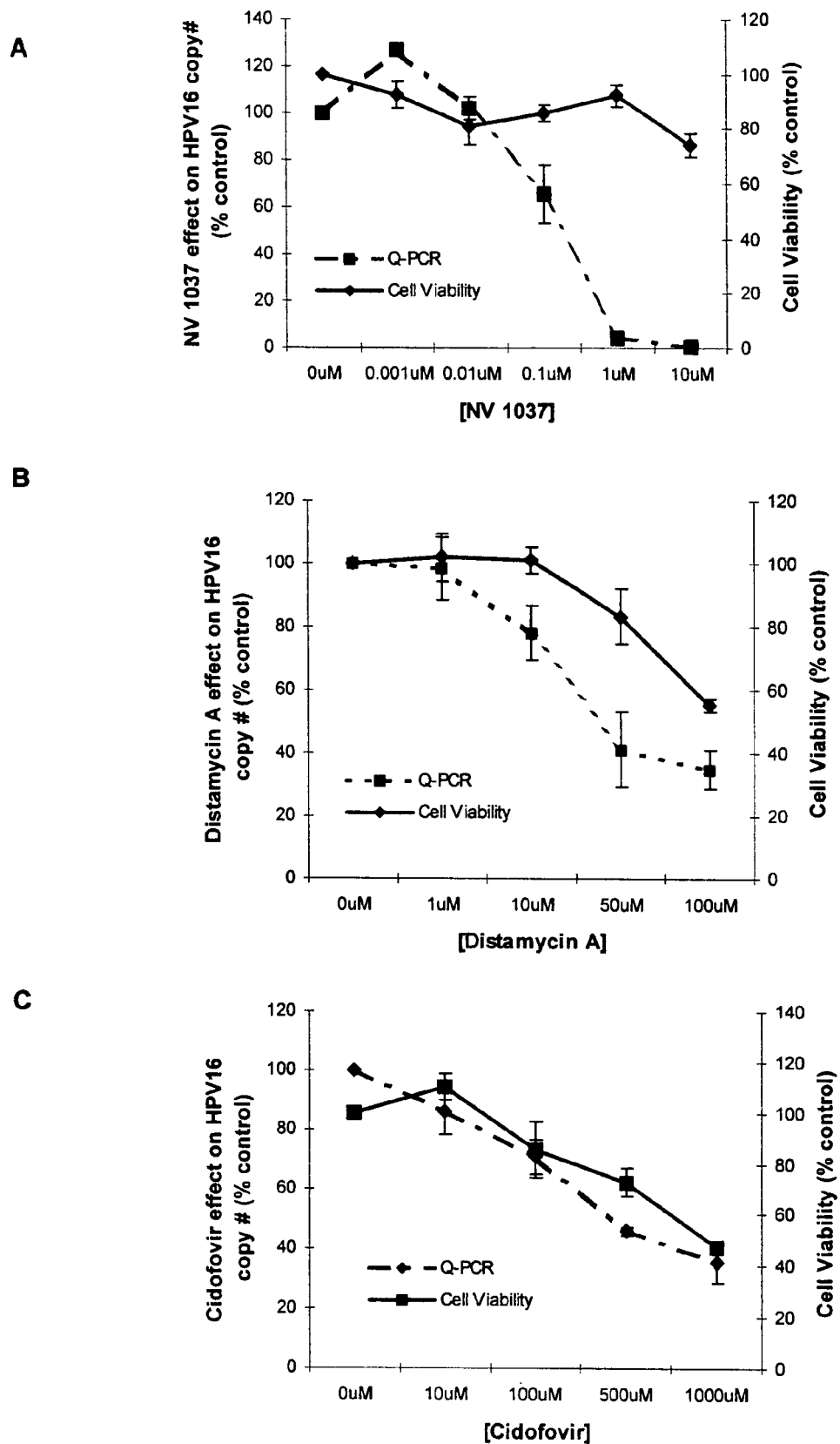

Polyamides were also found to be more potent than the naturally occurring polyamides, netropsin and distamycin, and, unlike netropsin and distamycin, had little effect on cell viability (FIG. 5). FIG. 5 compares the relative effects of 1037, distamycin A and cidofovir on HPV viral DNA and cell viability. Polyamide 1037 shows dramatic reduction of viral DNA levels at concentrations that have little impact on cell viability. Cidofovir and distamycin A are only effective against HPV DNA at high concentrations that also affect cell viability.

Example 4

Effect of Withdrawal of Polyamide on HPV16 Episodes

Figure 7:
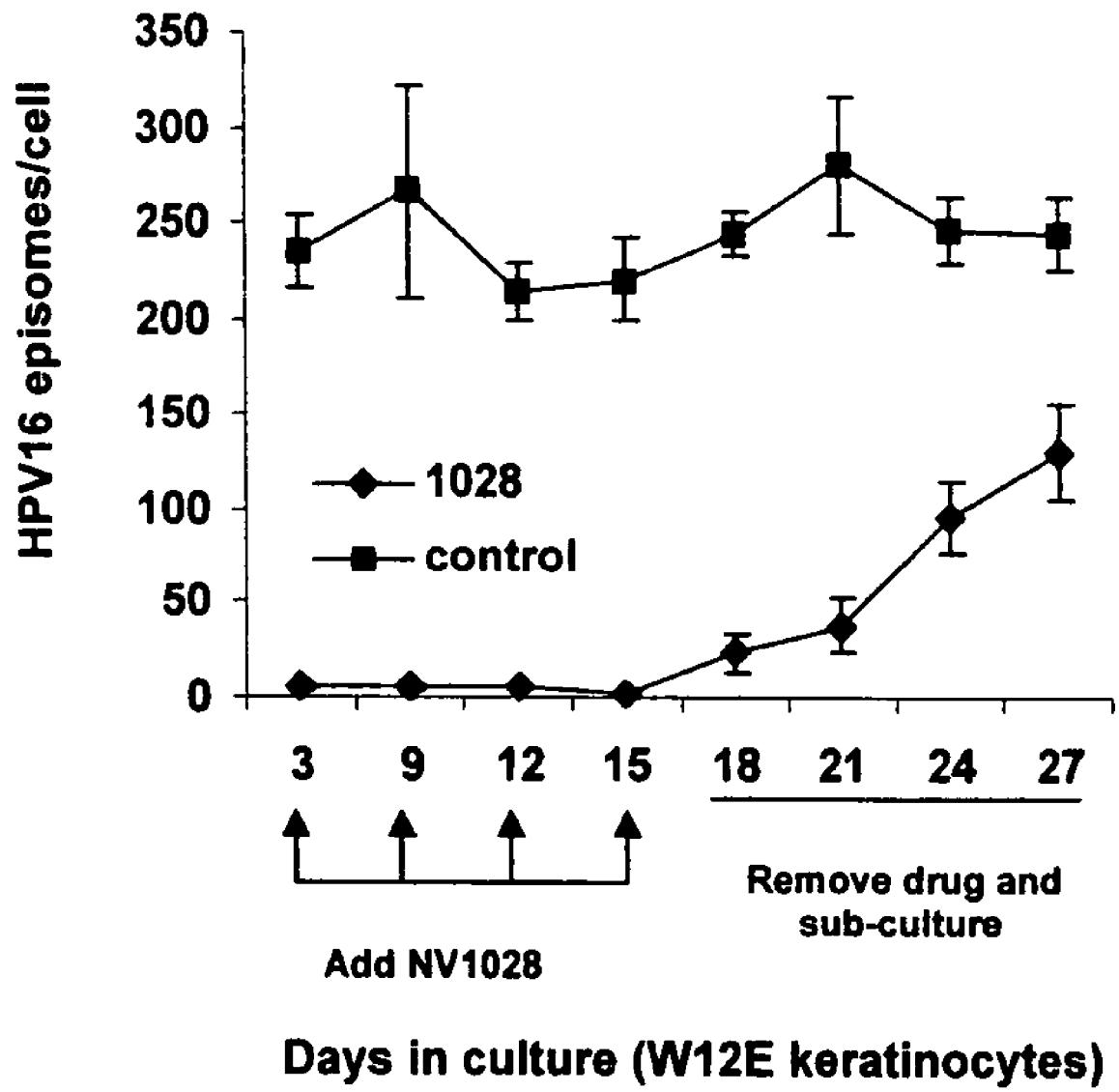

This experiment was performed to determine whether the decrease in HPV16 episodes in maintained after a polyamide is withdrawn from cells. Cells were plated on day 1 of experiment and 10 µM NV1028 added; cells were cultured for 3 days at which time cells were washed and fresh 1028 added; sub-culturing in the presence of 1028 was performed at the indicated days (x-axis) for 15 days; drug was washed out on day 17 and cells were sub-cultured in the absence of drug for 2 weeks to check for HPV16 episomal DNA rebound. Control W12E cells received 0.1% DMSO. FIG. 7 shows that HPV episomal DNA rebounds somewhat when a polyamide is withdrawn, but recovery does not approach control levels for at least two weeks after polyamide withdrawal.

Example 5

Control of Cellular Uptake and Nuclear Localization for Polyamides

As described above, polyamides of this invention readily localize to the nucleus of keratinocytes. However, in other cell types, including various transformed cells, polyamides often localize within vesicular compartments following treatment of cells. Polyamide uptake and cellular distribution were obtained by studying the effects of overall polyamide charge and acidity, and the influence of multi-drug resistance inhibitors on uptake (Crowley et al., Bioorg. Med. Chem. Lett., 13, 1565-70, 2003).

The studies revealed that BODIPY-labeled polyamides accumulate in acidic vesicles, mainly lysosomes, in the cytoplasm of mammalian cells. This is a phenomenon observed with many drugs and compounds that are mild bases. Verapamil, an agent that disrupts acidic vesicle homeostasis, blocked vesicular accumulation and led to nuclear accumulation of the BODIPY-labeled polyamide. These results suggest that the basic amine group commonly found at the end of synthetic polyamide chains is responsible for their accumulation in cytoplasmic vesicles in mammalian cells. In support of this suggestion, we found that modifying the charge on a polyamide by replacing the BODIPY moiety on the amine tail with a fluorescein moiety generated a new molecule that did not accumulate in cytoplasmic vesicles but rather localized to the nucleus of the cell.

Since nuclear DNA is the polyamide target, polyamides may indeed be useful compounds for regulating gene expression in mammalian cells when one of the two strategies outlined here, is used to target polyamides to the nucleus (Crowley et al., Bioorg. Med. Chem. Lett., 13, 1565-70, 2003). (See Best et al., Proc. Natl. Acad. Sci. USA, 100, 12063-68, 2003; Edelson et al., Nucl. Acids Res., 32: 2802-18, 2004).

Example 6

Identification of Polyamides for HPV 18

DNA-binding polyamides of this invention are directed against HPV16 that potently and dramatically decrease virus episomal DNA levels in human keratinocytes. Here we describe approaches to finding antiviral agents for HPV18. In one approach, the manner in which HPV is tethered to the host chromosomes will be used to target HPVs.

Polyamides are prepared by literature methods (e.g. Belitsky et al., Bioorg. Med. Chem., 10, 2767-74, 2002), and the method described in Example 8 below, using building blocks synthesized in-house. These include solid phase, such as Merrifield synthesis, and solution methods. All final products will be purified by HPLC to >98% purity, then aliquotted, lyophilized and stored frozen until use. The ability of polyamides to bind their nominal DNA targets, will be assessed by BIAcore analysis. Sufficient quantities are prepared for preliminary toxicity.

The design of polyamides to target A/T-rich regions of HPV18 is based on the four known recognition rules. The β-alanine, γ-turn and amino tail all recognize nucleotides A or T, and imidazole recognizes G. Three important aspects of the polyamides effective against HPV include: (1) polyamide sequences that result in clearance of HPV18; (2) Discovery of polyamide lengths that balance efficacy and uptake; (3) Discovery of where β-alanine groups are best incorporated in the polyamide.

TABLE 5

Polyamides for HPV 18.

| | | |
|---|---|---|
| 1 | ImPPI-γ-PPPPP-β-Dp | 8 base pairs |
| 2 | ImPPPPIPPPPI-γ-PPPPPPPPPP-β-Dp | 13 base pairs |
| 3 | ImPPPPPIPPP-γ-PPPPPPPPPP-β-Dp | 13 base pairs |
| 4 | ImPPPPPPPIPPPP-γ-PPPPPPPPPPPP-β-Dp | 16 base pairs |
| 5 | ImPPPPPPPPIPPPPP-γ-PPPPPPPPPPPPPP-β-Dp | 17 base pairs |
| 6 | Im-P-I(P)$_{10}$-γ-(P)$_{14}$-β-Dp | 17 base pairs |
| 7 | Im-(P)$_{10}$-γ-(P)$_{11}$-β-Dp | 14 base pairs |

All of the polyamides shown in Table 5, with the exception of compound 1, are quite long. Versions of each polyamide are prepared with beta-alanines (β) incorporated to relieve strain in the polyamide backbone due to slight imperfections that show up in the fit to DNA with these lengthy molecules. There are no set rules about where β-alanines should be placed, except that they interact unfavorably with G. A representative set of example variations in polyamide composition is given in Table 6, with one added β on either side of the γ-turn.

TABLE 6

Polyamide sequences based on one compound modified with β-alanine.

Im-PPP-β-PPP-β-IPPP-β-PP-γ-PPP-β-PPP-β-PPP-β-PPP-β-Dp
Im-PPPP-β-PPPI-β-PPP-β-P-γ-PPPP-β-PPP-β-PPPP-β-P-β-Dp
Im-β-PPPP-β-PPIP-β-PPP-β-γ-P-β-PPPPP-β-PPP-β-PPP-β-Dp
Im-P-β-PPPP-β-PIPP-β-PPP-γ-β-PPP-β-PPPP-β-PPP-β-P-β-Dp

In addition, truncated versions of the polyamides are prepared and tested. This may improve uptake and will help determine parameters for predicting length vs. selectivity. Examples of truncated polyamides based on polyamide 5, one of the two longest polyamides in Table 5, are given in Table 7.

TABLE 7

Truncated Polyamides recognizing one less base pair (bp) per entry
Shorter analogs of "parent" polyamide

| | |
|---|---|
| ImPPPPPPPPIPPPPP-γ-PPPPPPPPPPPPPP-β-Dp | One base pair shorter |
| ImPPPPPPPIPPPP-γ-PPPPPPPPPPPP-β-Dp | Two base pairs shorter |
| ImPPPPPPPIPPP-γ-PPPPPPPPPP-β-Dp | Three base pairs shorter |
| ImPPPPPPPIPP-γ-PPPPPPPPP-β-Dp | Four base pairs shorter |

The polyamide compounds of the invention are also useful as tools to probe the HPV life cycle.

Human keratinocytes, including those maintaining HPV episodes, are cultured on mitomycin C-treated J2 3T3 cells in media containing three parts Dulbecco's modified Eagle medium (DMEM) and one part F12 media, our modification of published methods (Rheinwald and Green, 1975). Media (E Media) is supplemented with 0.4 μg/mL hydrocortisone, 10 ng/mL cholera toxin, 5 μg/mL insulin, 24 μg/mL adenine, 5 μg/mL transferrin, 5 μg/mL 3,3, 5-triiodo-thyronine (T$_3$), 10 ηg/mL epidermal growth factor (EGF), 1% penicillin-streptomycin, and 5% fetal bovine serum (FBS). All cells are passaged at 70% confluency at a split ratio of 1:5.

Polyamides for HPV18 are dissolved at 10 mM in 100% DMSO and diluted with H$_2$O to 1 mM. Polyamides are added to cells in E media at final concentrations of 0.1-10 μM, with final DMSO concentrations of 0.1%. As controls, cells are incubated with normal E media and E media containing the "vehicle" 0.1% DMSO. The HPV DNA levels are then quantified according to previously published procedures (Garner-Hamrick and Fisher, Virology, 301, 334-41, 2002). After incubation, cells are harvested from the plates by either trypsinization or direct lysis with proteinase K digestion buffer (PK buffer: 100 mM NaCl, 10 mM Tris pH 8, 25 mM EDTA, 0.5% SDS, 0.1 mg/mL proteinase K). Trypsinized cells are counted on a hemocytometer and pelleted by centrifugation. Episomal HPV is isolated by the Hirt method (Hirt, 1967) and cell pellets are lysed in 0.6% SDS with 10 mM EDTA. NaCl is next added to a final concentration of 1 M. Following an overnight incubation at 4° C., precipitates containing the chromosomal DNA are spun down and episomal DNA precipitated by the addition of isopropanol. Cells lysed directly in PK buffer are transferred to microfuge tubes and incubated at 50° C. for 2 h. Lysates are then extracted with phenol/chloroform/isoamyl alcohol and spun through a phase lock gel (Eppendorf, Hamburg, Germany). Total DNA is then precipitated with 0.3 M NaOAc and 2.5 vol. ethanol and resuspended in Tris-EDTA (TE) buffer.

Viral DNA levels are next quantified according to variations on our previously published methods (Garner-Hamrick and Fisher, Virology, 301, 334-41, 2002). Quantitative PCR is performed using Real-Time PCR technology on an ABI PRISM 7700 Sequence Detector. All primers and probes were designed using Primer Express 1.0 (ABI). For HPV18, PCR primer-probe sets were designed within the L1 gene: sense 5'-TTTGGTTCAGGCTGGATTGC (SEQ.ID. NO. 3), antisense 5'-GCAGATGGAGCAGAACGTTTG (SEQ.ID. NO. 4), probe 5'-TCGCAAGCCCACCATAGGCCC (SEQ.ID. NO. 5). HPV31 primers-probe sets for PCR were also designed within the L1 gene: sense 5'-CTGCTATTTTG-GAAGATTGGAAT (SEQ.ID. NO. 6), antisense 5'-GGCCT-GTGAGGTGACAAACC (SEQ.ID. NO. 7), probe 5'-TTG-GATTGACCACACCTCCCTCAGGTT (SEQ.ID. NO. 8).

All primers and probes are synthesized and HPLC purified by Applied Biosystems (Foster City, Calif.). The HPV probes are labeled with the 5' reporter dye FAM (6-carboxy-fluorescein) and the 3' quencher dye TAMRA (6-carboxytetramethyl-rhodamine). A standard curve is generated using a range of $10^8$ to 10 copies/reaction of cloned, genomic HPV31 or HPV18 DNA using the following formula: $(1.82 \times 10^{15})$ (μg/μL stock DNA)/(length in base pairs)(2)=copies/μL stock DNA. PCR reactions contain final concentrations of 1X Universal Master Mix (PE Applied Biosystems), 200 ηM of each primer, and 250 ηM probe (PE Applied Biosystems) in a reaction volume of 25 μL. Each Hirt-isolated DNA sample is analyzed in triplicate reactions for episomal HPV. Copies/reaction are determined from the standard curve, and copies/cell determined according to the following formula: (copies/reaction)(DNA dilution)/(total # cells)=copies/cell.

Example 7

Initial in vitro Toxicity Assessments

Polyamides that significantly reduce HPV18 DNA levels can be further tested in a series of follow up studies. The follow up studies will require re-preparation of the polyamides on a larger scale.

Southern blotting is used to confirm the effects of polyamides on HPV18 DNA levels that were determined using real-time PCR technology. The experiments are conducted as previously described (Gamer-Hamrick and Fisher, Virology, 301, 334-41, 2002). Briefly, 5 μg of total cell DNA from both polyamide-treated and control cells is digested with BamHI and run on a 0.7% agarose gel. After transfer to Nytran (Schleicher & Scheull, Keene, NH), the DNA is probed with gel purified full-length HPV 18 that has been liberated from pUC19 with BamHI, and randomly primed in the presence of DIG-UTP (Roche). Following incubation with anti-DIG AP (alkaline phosphatase), HPV DNA is detected with ECF substrate and phosphor-imaging. The experiments should confirm the Taqman™ assay results, and they provide an independent, orthogonal assay of activity.

Secondly, 50% and 90% effective concentration values ($EC_{50}$ & $EC_{90}$) are determined for each polyamide over a dose range of 10 ηM to 50 μM (10 ηM, 100 ηM, 500 ηM, 1 μM, 5 μM, 10 μM, and 50 μM) using Taqman data. Previous studies of ours indicate that this range should provide suitable dose-response curves. The final levels of HPV DNA per cell are determined for each polyamide concentration, and data is expressed as % inhibition relative to vehicle-treated controls. $EC_{50}$s are then calculated using nonlinear regression analysis with Sigmaplot software.

The toxicity of each polyamide found active against HPV18 is monitored in normal human keratinocytes using an MTT cell viability assay (Denizot and Lang, 1986). Polyamides are initially supplied to normal keratinocytes in growth media at concentrations of 10 ηM, 100 ηM, 1 μM, 10 μM, 100 μM, 500 μM, 1 mM and 10 mM. Each set of samples is supplied in triplicate, in clear 96-well plates. A tetrazolium dye (3-[4,5-dimethylthiazol-2-yl]-2,5-diphenyl tetrazolium bromide or MTT, Sigma) is added to the cell cultures 48 hours after addition of polyamides. After 4 hours cells are rinsed 1X with PBS, and isoproanol containing 0.04N HCl is added to lyse cells and solubilize MTT formazan. Plates are read on a plate reader at a test wavelength of 570 ηm and a reference wavelength of 630 ηm. Data are expressed as % inhibition of vehicle-treated controls and, as for analysis of effects on HPV DNA levels, $IC_{50}$s are calculated using nonlinear regression analysis with Sigmaplot software.

The selectivity index for each effective polyamide is then determined as the ratio of the $EC_{50}$ to the $IC_{50}$ (SI=$EC_{50}$/$IC_{50}$). An SI of 5 is considered an acceptable starting point.

Finally, the effects of multiple dosing with polyamides are followed in vitro. The purpose of these studies is to gauge the extent to which polyamides can clear cells of episomal DNA in the absence of an immune system. While it is recognized that, in general, an intact immune system is important for optimal antiviral effects, these studies are important to help prioritize and select compounds designed to clear viral DNA in animal studies. Since typical clinical antiviral regimens last from 1 to 2 weeks or longer, we can dose HPV18-positive keratinocytes for 6, 9, and 12 days by providing fresh polyamide with each change of medium. The HPV-18 keratinocytes are passaged during the course of these experiments as needed. Dosage can be at levels >$EC_{90}$ value as long as those concentrations previously showed no significant toxicity. Treated cells are then collected for Taqman analysis and also re-plated in fresh media. The re-plated cells are allowed to recover for an additional 7 days at which time they are harvested and viral DNA content analyzed by Taqman. The viral DNA content of the recovered cells is then compared with that of the cells at the end of the treatment regiment.

The data for HPV show a remarkable and potent reduction in viral DNA levels. However, it is important to note that the recovery or "rebound" of viral DNA occurs after a single 48 hr. treatment. Polyamides were removed from culture at 48 hrs, but the HPV DNA levels and subsequent "rebound" occurred many days later. Therefore, if all of the original polyamide dose were still present in the cells at day 6, it would have been diluted by a factor of at least four due to cell doubling. Since most antiviral regimens last at least 7 to 14 days (and may last for months), we anticipate that the longer, multiple dosing approach described here will reduce the ability of HPV to recover in vitro following treatment, and we anticipate that some polyamides may result in clearance of HPV DNA.

Example 8

Methods for Preparation of Poly-N-methylimidazole-N-methylpyrrole Polyamides and Analogs that Lack a β-Alanine Between the C-terminal Heterocycle and the C-terminal Cationic End Group One method of synthesis is to prepare a polyamide oligomer starting with Boc-β-alanine-WANG solid phase synthesis resin, adding building blocks as required for the target sequence. Preparing free carboxylic acids at the C-terminus of polyamides allows polyamide molecules to be further elaborated by solution-phase coupling into a variety of structures, including molecules that lack beta-alanine immediately adjacent to a C-terminal polar group such as the cationic group(s) derived from aliphatic di- and triamines. Wang resins, especially in the form Fmoc-β-alanine-Wang, are useful for this chemistry. These resins include, for example, the trifluoroacetic acid-cleavable Novabiochem® materials know as NovaSyn® TG HMP, NovaPeg Wang, HMPA-PEGA and HMPA NovaGel™ resins.

The polyamide is cleaved from the resin with trifluoroacetic acid. After cleaving a polyamide from its Wang or Wang-like resin by trifluoroacetic acid, trifluoroacetate is removed from the product prior to coupling the C-terminal carboxylate and a new amine to generate a C-terminal amide. In general, lyophilization and/or ion exchange may be used to remove trifluoroacetic acid or its anion prior to an amide coupling reaction to elaborate the polyamide. Additionally, ion exchange to make the hydrochloride (or similar) salt of a cationic polyamide is preferred prior to amide bond formation.

The resultant free carboxylic acid at the C-terminus is then reacted in solution with molecules built from standard components for polyamides that recognize DNA, except that an aliphatic beta-amino acid is not located immediately adjacent to the C-terminal cationic group.

Suitable examples of C-terminal amines include the following structures.

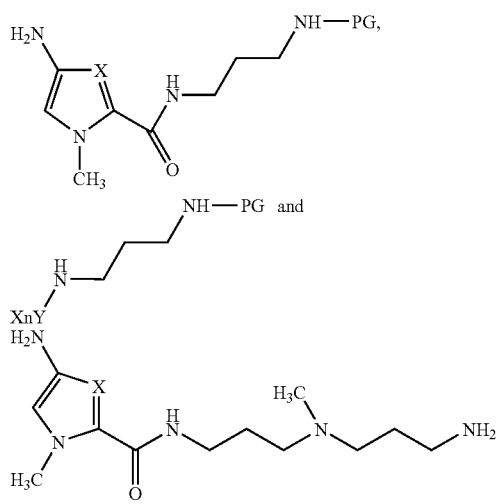

wherein X=CH, N; PG=a protecting group stable to the necessary amide bond forming conditions. Examples of suitable protecting groups include FMOC, Boc and TBDMS.

Polyamide compounds were verifed with MALDI mass spec after each unit was added. The measurements were performed at Peptides International (Louisville Ky.). Polyamides were purified to 98% or better purity by preparative HPLC (sometimes requiring a second prep HPLC run). HPLC fractions were combined to give final product after analytical HPLC and mass spectra (MALDI) showed both the presence of the final product and the absence of failure sequences.

All references cited herein are incorporated by reference in their entirety.

OTHER EMBODIMENTS

It is to be understood that while the invention has been described in conjunction with ailed description thereof, the foregoing description is intended to illustrate and not limit pe of the invention, which is defined by the scope of the appended claims. Other advantages, and modifications are within the scope of the following claims.

What is claimed is:

1. A compound selected from the group consisting of
ImPPβPIPβPPγ(NH$_2$)PPβPPPβPPPβTa;
F$_3$CC(O)PPβPPβPIγ(NH$_2$)PβPPβPPPβPβTa;
F$_3$CC(O)PPβPPβPγ(NH$_2$)PPPβPPPβPβTa;
ImPPβPPPγ(NH$_2$)PPβPPPPβTa;
ImPPPβPPβγPPβPPPβPβTa;
ImPPPβPPβγ(NH$_2$)PPβPPPβPβTa;
ImPPPβPPPγPPPβPPPββTa;
ImPPβPPPγPPβPPPPβTa;
ImPPPβPPβγ(NH$_2$)PPβPPPβPβDp;
ImPPPβPPβPPPγ(NH$_2$)PPPβPPPβPPPβDp; and
ImPPPβPPβPPPγPPPβPPPβPPPβDp.

2. A pharmaceutical composition comprising a therapeutically effective amount of a compound of any of claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,589,171 B2 |
| APPLICATION NO. | : 11/800105 |
| DATED | : September 15, 2009 |
| INVENTOR(S) | : James K. Bashkin et al. |

It is certified that error appears in the above-identified patent and that said Letters Patent is hereby corrected as shown below:

In the Specification

Column 1, line 16, in the section entitled "FEDERALLY SPONSORED RESEARCH OR DEVELOPMENT"

delete:

"Grant Number R41 AI062182"

And substitute the following:

Grant Number R4I AI062182

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 7,589,171 B2 | |
| APPLICATION NO. | : 11/800105 | |
| DATED | : September 15, 2009 | |
| INVENTOR(S) | : James K. Bashkin et al. | |

It is certified that error appears in the above-identified patent and that said Letters Patent is hereby corrected as shown below:

In the Specification

Column 1, line 16, in the section entitled "FEDERALLY SPONSORED RESEARCH OR DEVELOPMENT"

delete:

"Grant Number R41 A1062182"

And substitute the following:

Grant Number R41 AI62182

This certificate supersedes the Certificate of Correction issued October 14, 2014.

Signed and Sealed this
Twenty-fourth Day of March, 2015

Michelle K. Lee
*Director of the United States Patent and Trademark Office*